(12) United States Patent
Herr et al.

(10) Patent No.: US 9,976,984 B2
(45) Date of Patent: May 22, 2018

(54) FREE-STANDING MICROFLUIDIC GEL ELECTROPHORESIS DEVICES AND METHODS

(71) Applicant: The Regents of the University of California, Oakland, CA (US)

(72) Inventors: Amy E. Herr, Oakland, CA (US); Todd Duncombe, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 442 days.

(21) Appl. No.: 14/271,309

(22) Filed: May 6, 2014

(65) Prior Publication Data

US 2014/0332383 A1 Nov. 13, 2014

Related U.S. Application Data

(60) Provisional application No. 61/822,198, filed on May 10, 2013.

(51) Int. Cl.
*G01N 27/453* (2006.01)
*G01N 27/447* (2006.01)

(52) U.S. Cl.
CPC . *G01N 27/44704* (2013.01); *G01N 27/44791* (2013.01)

(58) Field of Classification Search
CPC .......... G01N 27/447; G01N 27/44704; G01N 27/44743; G01N 27/44756; G01N 27/453; G01N 27/44791; C07K 1/26–1/285
See application file for complete search history.

(56) References Cited

U.S. PATENT DOCUMENTS

| | | | | |
|---|---|---|---|---|
| 4,018,662 A | * | 4/1977 | Ruhenstroth-Bauer | G01N 27/447 422/401 |
| 4,443,319 A | * | 4/1984 | Chait | G01N 27/44773 204/616 |
| 4,740,283 A | | 4/1988 | Laas et al. | |
| 4,790,919 A | * | 12/1988 | Baylor, Jr. | C08F 20/56 204/616 |

(Continued)

FOREIGN PATENT DOCUMENTS

| | | | | |
|---|---|---|---|---|
| EP | 0173081 A1 | * | 7/1985 | ............. G01N 27/26 |
| EP | 1217368 A1 | * | 12/2001 | ........... G01N 27/447 |
| WO | WO 00/60118 A2 | * | 10/2000 | ............... C12Q 1/68 |

OTHER PUBLICATIONS

EPO computer-generated English language translation of Marc Artigue EP 1217368 A1, downloaded Nov. 30, 2016.*

(Continued)

*Primary Examiner* — Alexander S Noguerola
(74) *Attorney, Agent, or Firm* — Bret E. Field; Rudy J. Ng; Bozicevic, Field & Francis LLP

(57) ABSTRACT

Provided are devices that include a support, a free-standing polymeric separation medium associated with the support and configured to separate a sample along a directional axis, and a sample-loading element associated with the polymeric separation medium. Systems that include the devices, as well as methods of using the devices, are also provided. Embodiments of the present disclosure find use in a variety of different applications, including detecting whether an analyte is present in a fluid sample.

26 Claims, 27 Drawing Sheets

(56) References Cited

U.S. PATENT DOCUMENTS

| | | | |
|---|---|---|---|
| 4,828,670 A * | 5/1989 | Sarrine | G01N 27/44782 |
| | | | 204/616 |
| 5,047,135 A * | 9/1991 | Nieman | G01N 27/44782 |
| | | | 204/619 |
| 5,080,769 A | 1/1992 | Fassett et al. | |
| 5,750,015 A | 5/1998 | Soane et al. | |
| 6,090,256 A * | 7/2000 | Kadokami | G01N 27/44704 |
| | | | 204/606 |
| 6,964,735 B2 | 11/2005 | Soane et al. | |
| 7,597,791 B2 | 10/2009 | Huang et al. | |
| 2001/0044108 A1 * | 11/2001 | Shih | G01N 27/44717 |
| | | | 435/6.18 |
| 2010/0084270 A1 | 4/2010 | Vulto et al. | |

OTHER PUBLICATIONS

Gel-Fix™/NetFix™ Technical Notes by Serva Electrophoresis, publication date unkown, downloaded Aug. 22, 2017 from http://www.serva.de/www_root/documents/TN_GelNetFix.pdf.*

Tegelström et al., "Silanization of supporting glass plates avoiding fixation of polyacrylamide gels to glass cover plates," Electrophoresis 1986, 7, 99 (one page article).*

* cited by examiner

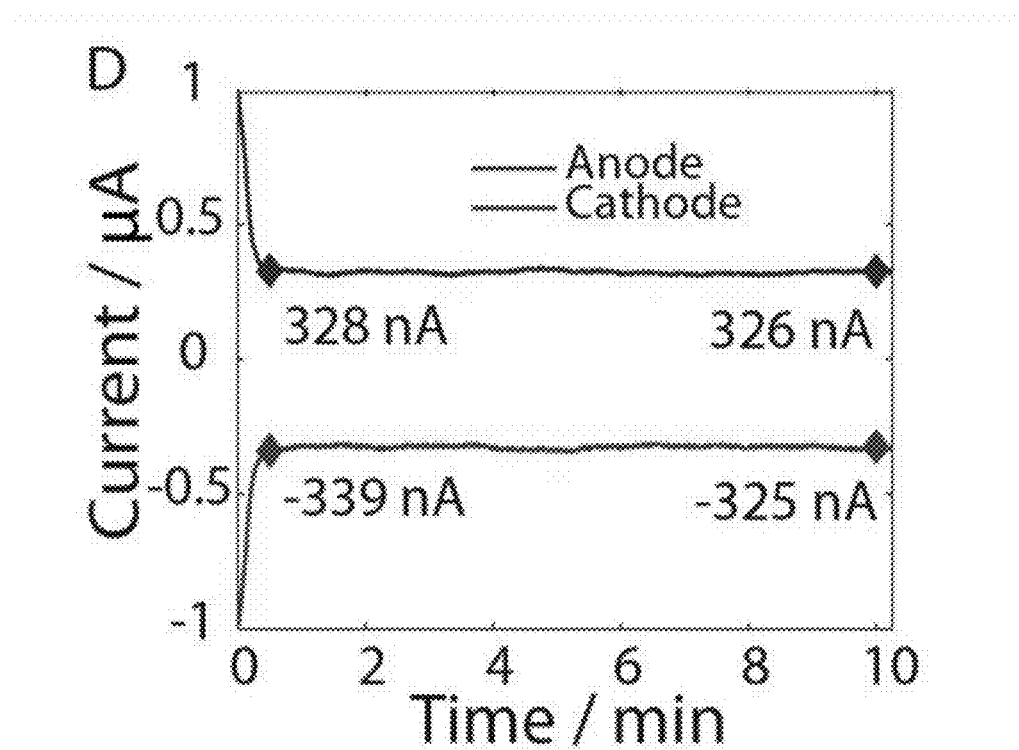
FIG. 3, continued

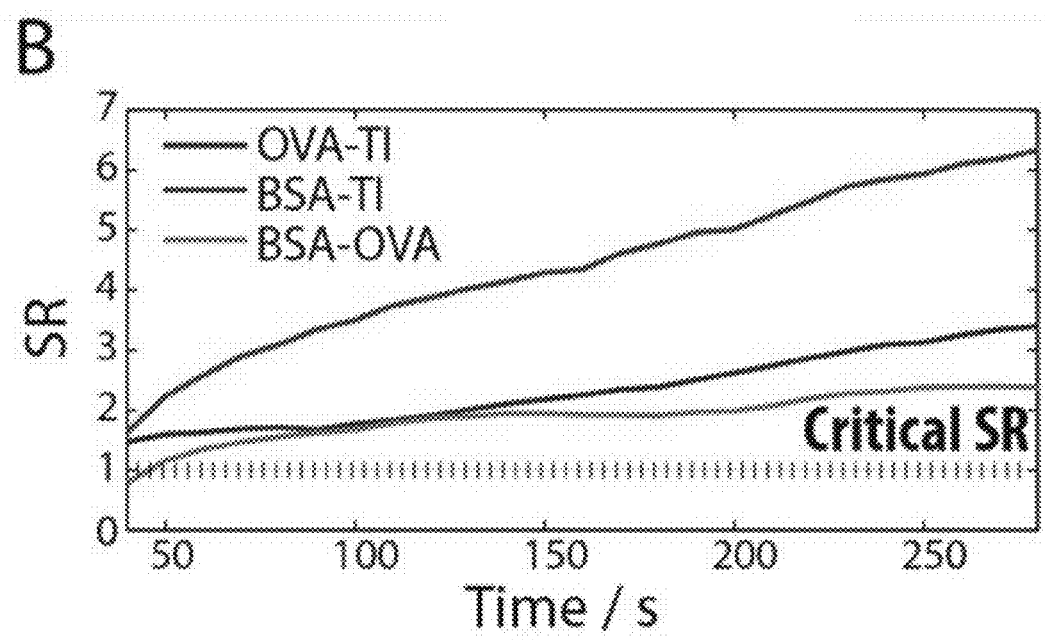
FIG. 4, continued

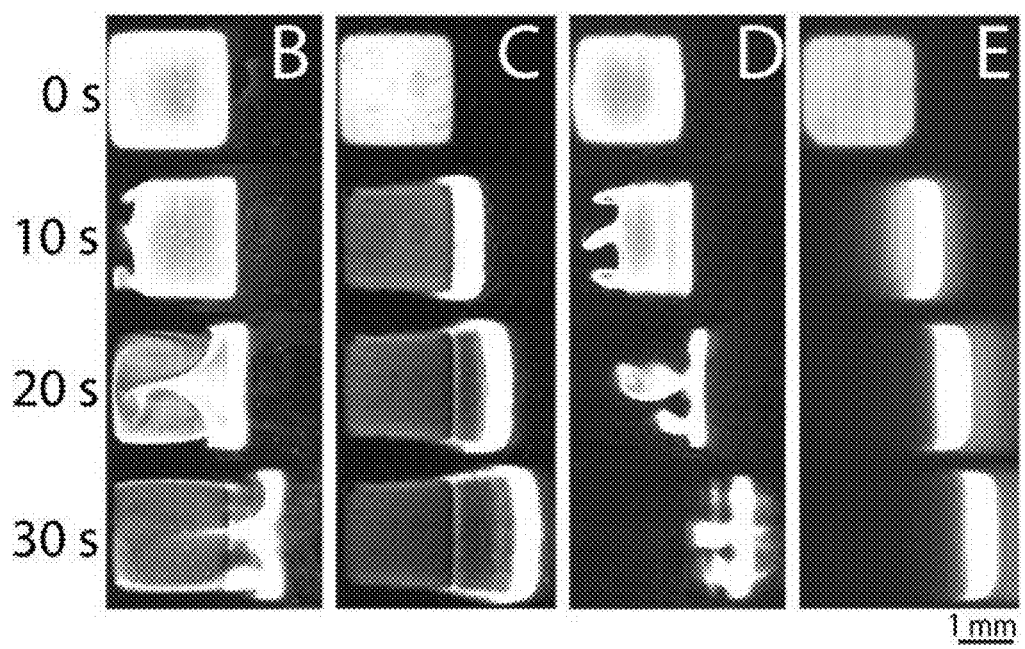
FIG. 7, continued

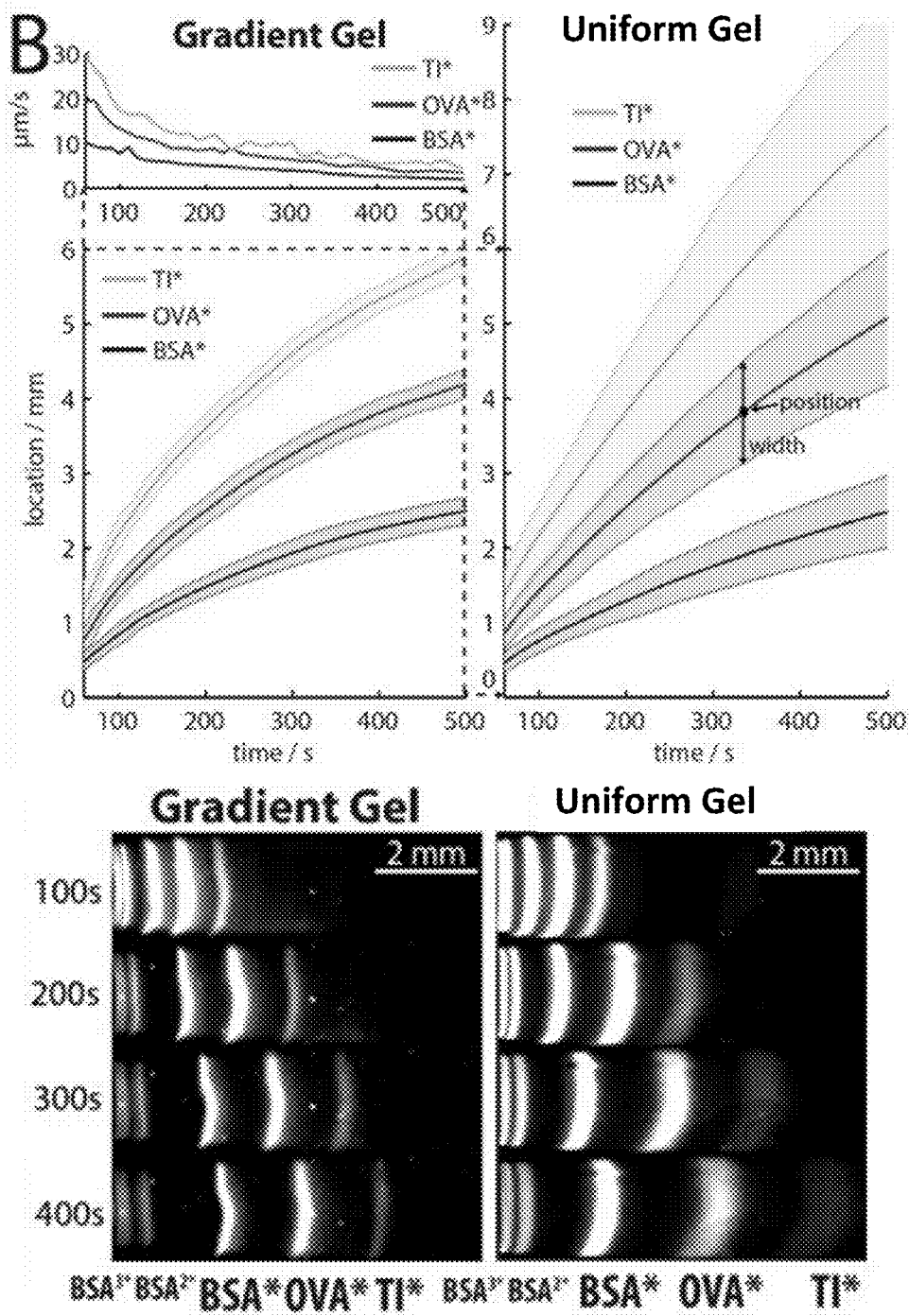
FIG. 9, continued

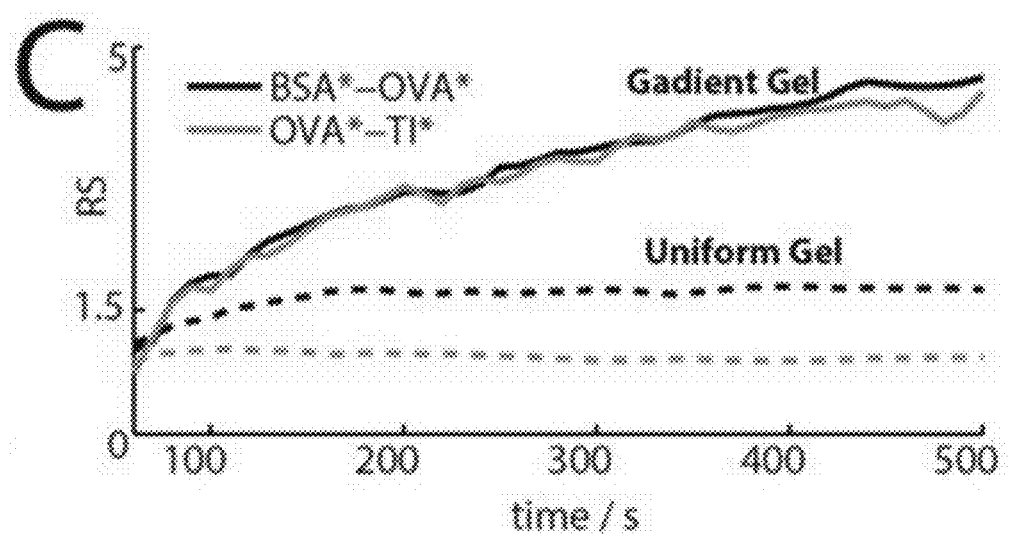
FIG. 9, continued

FREE-STANDING MICROFLUIDIC GEL ELECTROPHORESIS DEVICES AND METHODS

CROSS-REFERENCE TO RELATED APPLICATION

Pursuant to 35 U.S.C. § 119(e), this application claims priority to the filing date of U.S. Provisional Application No. 61/822,198, filed May 10, 2013, the disclosure of which is incorporated herein by reference.

INTRODUCTION

Recently advances have improved slab-gel electrophoresis performance. For example, the concurrent separation of tens or hundreds of proteins is possible of some slab-gel electrophoresis systems. In contrast to slab-gel based systems, microfluidic electrophoresis systems reduce the amount of sample required and provide for high efficiency separations. Typical microfluidic technologies are miniaturized platforms that include enclosed microchannels. In microchannel electrochromatography, the high surface area to volume ratio results in efficient heat dissipation enabling the application of high electric fields for rapid separations. Microfluidic protein separations can perform better than slab-gel polyacrylamide gel electrophoresis (PAGE) systems in terms of assay speed and multiplexing. However, electrochromatography in closed microchannels may pose difficulties for subsequent extraction and downstream processing of the sample following separation of the sample constituents.

SUMMARY

Provided are devices that include a support, a free-standing polymeric separation medium associated with the support and configured to separate a sample along a directional axis, and a sample-loading element associated with the separation medium. Systems that include the devices, as well as methods of using the devices, are also provided. Embodiments of the present disclosure find use in a variety of different applications, including detecting whether an analyte is present in a fluid sample.

Embodiments of the present disclosure include a device. The device includes a support, a free-standing polymeric separation medium associated with the support and configured to separate a sample along a directional axis, and a sample-loading element associated with the polymeric separation medium.

In some embodiments, the separation medium includes a polymeric gel.

In some embodiments, the sample-loading element includes one or more walls defining an interior space of the sample-loading element. In some embodiments, the polymeric separation medium and the walls of the sample-loading element are contiguous and include the same material. In some embodiments, the walls of the sample-loading element include a polymeric gel.

In some embodiments, the device includes two or more free-standing polymeric separation media associated with the support and two or more sample-loading elements associated with the two or more free-standing polymeric separation media.

Embodiments of the present disclosure include a method of detecting an analyte in a fluid sample. The method includes introducing the fluid sample into a microfluidic device. The microfluidic device includes a support, a free-standing polymeric separation medium associated with the support and configured to separate the sample along a directional axis, and a sample-loading element associated with the polymeric separation medium. The method also includes directing the sample through the polymeric separation medium to produce a separated sample, and detecting the analyte in the separated sample.

In some embodiments of the method, the directing includes applying an electric field to the polymeric separation medium.

In some embodiments of the method, the detecting includes labeling the analyte in the separated sample.

In some embodiments, the method further includes contacting the separated sample with one or more secondary reagents. In some embodiments, the contacting includes one or more of diffusion, electrokinetic transport and hydrodynamic transport. In some embodiments, the one or more secondary reagents are selected from an affinity probe, a dye, an antibody, an enzyme, an enzyme substrate and a nucleic acid.

Embodiments of the present disclosure include a system that includes one or more devices and a detector. Each device includes a support, a free-standing polymeric separation medium associated with the support and configured to separate a sample along a directional axis, and a sample-loading element associated with the polymeric separation medium.

In some embodiments, the polymeric separation medium includes a polymeric gel.

In some embodiments, the sample-loading element includes one or more walls defining an interior space of the sample-loading element. In some embodiments, the polymeric separation medium and the walls of the sample-loading element are contiguous and include the same material. In some embodiments, the walls of the sample-loading element include a polymeric gel.

In some embodiments, the system comprises one or more regions of devices, wherein each region includes two or more devices. In some embodiments, the devices in each region are contiguous and include the same material. In some embodiments, the devices in each region are arranged in series. In some embodiments, the system includes two or more regions of devices arranged in parallel.

In some embodiments, the detector is a photomultiplier tube, a charge-coupled device, an intensified charge-coupled device, a complementary metal-oxide-semiconductor sensor, visual colorimetric readout, or a photodiode.

In some embodiments, the system further includes a chamber configured to substantially maintain the ambient humidity around the microfluidic devices.

Embodiments of the present disclosure include a kit that includes a microfluidic device and a packaging configured to contain the device. The microfluidic device includes a support, a free-standing polymeric separation medium associated with the support and configured to separate a sample along a directional axis, and a sample-loading element associated with the polymeric separation medium.

BRIEF DESCRIPTION OF THE FIGURES

FIGS. 7A-7E show images illustrating that electroosmotic flow (EOF) suppressors minimized injection dispersion from the free-solution reservoir. FIG. 7A shows an image of the motion of fluorescent beads in a 2 mm×2 mm solution-filled reservoir (left), which showed the formation of two axially symmetric vortices driven by EOF. A time-lapse montage (right, 7 s between frames) of bead transport shows the dependence of flow on the applied voltage. FIG. 7B shows an image of discontinuous electrophoresis injection of protein (500 nM OVA* in 150 mM Tris-HCl), which was distorted by EOF. FIG. 7C shows an image, which shows that while homogeneous electrophoretic injections resulted in the desired axially orthogonal protein bands, streaking from the reservoir resulted in injection dispersion and sample mass loss. By adding an EOF suppressor, 0.5% Triton X-100, to the sample solution, protein adsorption was minimized for both discontinuous (FIG. 7D) and homogeneous (FIG. 7E) electrophoretic injections. E=100 V/cm, 15% T PAG.

FIG. 8A shows a graph of fluorescence (RFU) vs. migration distance (mm), where sample stacking was evaluated in 10% T, 15% T, and 20% T fsPAGs by electrophoretically loading a sample of 500 nM OVA* at 100 V/cm. The intensity plot profile for each gel density was displayed at 14 s in the first 1.5 mm of the PAG. FIG. 8B shows images of the separation in 15% T and 20% T fsFSPAG devices compared in the first 60 s of migration for a protein ladder. In the 20% T PAG (right), the BSA*-OVA* and OVA*-TI* species were fully resolved in 1 minute, with RS values of 1.3 and 1.0, respectively, while for the 15% T PAG (left), both separations were completed after more than 1 minute of elapsed separation time.

FIG. 9A shows an image (top) and a graph of relative intensity vs. location (mm) (bottom) for gradient fsPAGs fabricated using a PA density gradient beneath a gasket prior to photo-polymerization the gel. FIG. 9B shows graphs (top) and images (bottom) of gradient (10% T to 20% T) fsPAGE compared side-by-side with the uniform fsPAGE seen in FIG. 8B. Peak position and width of the protein samples were plotted over time for each condition, which showed the difference in dispersion over the course of a 500 s separation at 100 V/cm.

FIG. 21B (right) shows a graph of Log MW vs. Relative Mobility for BSA, OVA and TI.

DETAILED DESCRIPTION

Figure 1A:
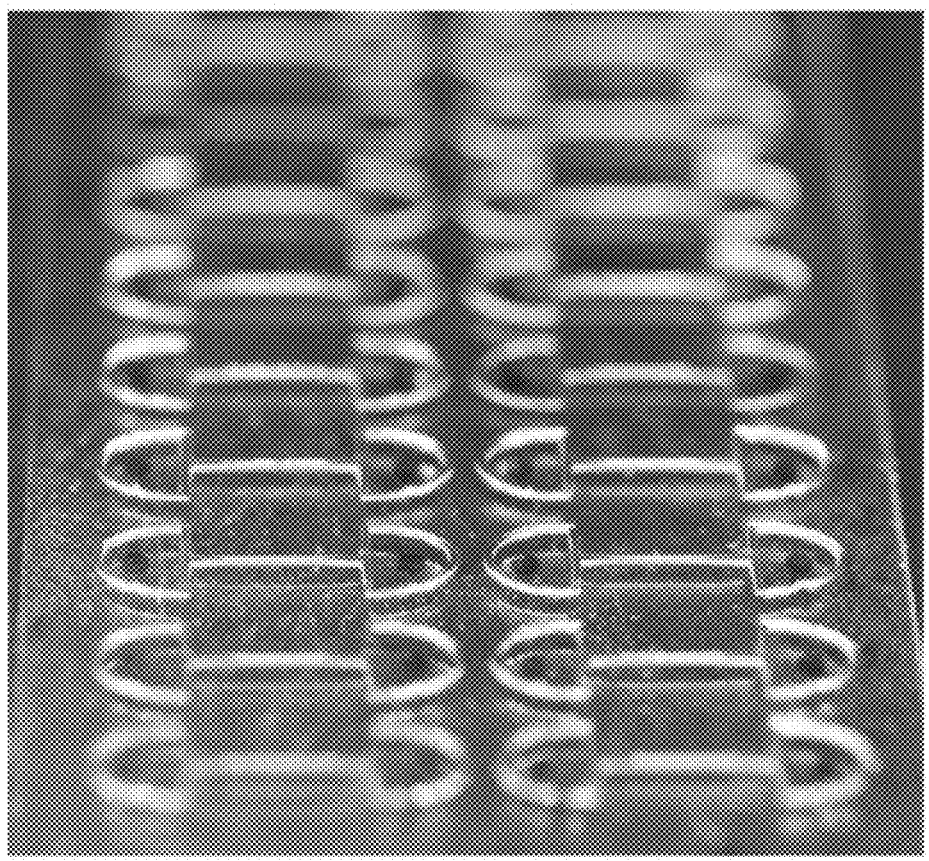
FIGS. 1A and 1B show photographs of free-standing polyacrylamide microchannel arrays, according to embodiments of the present disclosure.

Provided are devices that include a support, a free-standing polymeric separation medium associated with the support and configured to separate a sample along a directional axis, and a sample-loading element associated with the polymeric separation medium. Systems that include the devices, as well as methods of using the microfluidic devices, are also provided. Embodiments of the present disclosure find use in a variety of different applications, including detecting whether an analyte is present in a fluid sample.

Before the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges and are also encompassed within embodiments of the present disclosure, subject to any specifically excluded limit in the stated range. Where the stated range includes one or both of the limits, ranges excluding either or both of those included limits are also included in embodiments of the present disclosure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Below, the subject devices are described first in greater detail. Methods of detecting an analyte in a fluid sample are also disclosed in which the subject devices find use. In addition, systems and kits that include the subject devices are also described.

Devices

Embodiments of the present disclosure include a free-standing polymeric separation medium associated with a support. By "free-standing" is meant that the separation medium is associated with a support, such as disposed on the surface of the support. For instance, the polymeric separation medium may be disposed on the surface of a support such that only one surface (e.g., the bottom surface) of the separation medium is in contact with the surface of the support. In these instances, the sides of the polymeric separation medium (e.g., the sides of the separation medium extending up from the bottom of the separation medium) may not be in contact with a support, or a surrounding chamber (e.g., a microfluidic chamber) if present. Similarly, the top surface of the polymeric separation medium may not be in contact with a support, or the surrounding chamber (e.g., a microfluidic chamber) if present. In some instances, the free-standing polymeric separation medium may be disposed on the surface of a support and surrounded by the ambient environment. For example, the polymeric separation medium may have a bottom surface in contact with the support, where the sides of the separation medium and the top surface of the polymeric separation medium are exposed to the ambient environment. In certain embodiments, the free-standing polymeric separation medium may be disposed on the surface of a support and positioned inside an environmental chamber, such that the free-standing polymeric separation medium is surrounded by the environment provided inside the environmental chamber. In some instances, the polymeric separation medium may have a bottom surface in contact with the support, where the sides of the separation medium and the top surface of the separation medium are exposed to the environment inside the environmental chamber. For instance, the environmental chamber may contain an environment (e.g., an assay environment) that has a higher humidity than ambient conditions. An assay environment with a higher humidity may facilitate a reduction in evaporation of liquids (e.g., buffers, etc.) from the separation medium. In certain embodiments, a free-standing polymeric separation medium is disposed on a surface of a support, where the support does not form a channel, a trough or depression around the separation medium.

In certain embodiments, the polymeric separation medium is attached to the support. For example, the polymeric separation medium may be disposed on a surface of the support as described above, and the surface of the polymeric separation medium in contact with the surface of the support may be covalently bound to the surface of the support. In some instances, covalent bonds are formed between the polymeric separation medium and the support during a polymerization reaction that forms the polymeric separation medium. In some instances, the polymerization reaction is initiated by exposing the separation medium to light, e.g., ultraviolet (UV) light.

The polymeric separation medium may be configured to separate the analytes in a sample from each other. In some cases, the polymeric separation medium is configured to separate the analytes in a sample based on the physical properties of the analytes. For example, the polymeric separation medium may be configured to separate the analytes in the sample based on the molecular weight, size, charge (e.g., charge to mass ratio), isoelectric point, etc. of the analytes. In certain instances, the polymeric separation medium is configured to separate the analytes in the sample based on the molecular weight of the analytes. In some cases, the polymeric separation medium is configured to separate the analytes in the sample based on the isoelectric point of the analytes (e.g., isoelectric point focusing). The polymeric separation medium may be configured to separate the analytes in the sample into distinct detectable bands of analytes. By "band" is meant a distinct detectable region where the concentration of an analyte is significantly higher than the surrounding regions. Each band of analyte may include a single analyte or several analytes, where each analyte in a single band of analytes has substantially similar physical properties, as described above.

In certain embodiments, the polymeric separation medium is configured to separate the analytes in a sample as the sample traverses the polymeric separation medium. In some cases, the polymeric separation medium is configured to separate the analytes in the sample as the sample flows through the polymeric separation medium. In certain embodiments, the separation medium includes a polymer, such as a polymeric gel. The polymeric gel may be a gel suitable for gel electrophoresis. The polymeric gel may include, but is not limited to, a polyacrylamide gel, an agarose gel, and the like. The resolution of the polymeric separation medium may depend on various factors, such as, but not limited to, pore size, total polymer content (e.g., total acrylamide content), concentration of cross-linker, applied electric field, assay time, and the like. For instance, the resolution of the separation medium may depend on the pore size of the polymeric separation medium. In some cases, the pore size depends on the total polymer content of the separation medium and/or the concentration of cross-linker in the separation medium. In certain instances, the polymeric separation medium is configured to resolve analytes with molecular weight differences of 10,000 Da or less, such as 7,000 Da or less, including 5,000 Da or less, or 2,000 Da or less, or 1,000 Da or less, for example 500 Da or less, or 100 Da or less. In some cases, the polymeric separation medium may include a polyacrylamide gel that has a total acrylamide content of ranging from 1% to 50%, such as from 1% to 40%, including from 1% to 30% (% w/v).

In certain embodiments, the polymeric separation medium is configured to be formed from precursor moieties. For example, the separation medium may be a gel (e.g., a polyacrylamide gel) formed form gel precursors (e.g., polyacrylamide gel precursors, such as polyacrylamide gel monomers). The precursor moieties may be configured to react to form the separation medium. For instance, the gel precursors may be configured to react with each other to form the polyacrylamide gel separation medium. The reaction between the gel precursors may be activated by any suitable protocol, such as, but not limited to, chemical activation, light activation, etc. In some embodiments, the gel precursors are configured to be activated chemically, for example by contacting the gel precursors with an activation agent, such as, but not limited to, a peroxide. In some embodiments, the gel precursors are configured to be activated by light (i.e., photo-activated), for instance by contacting the gel precursors with light. The light may be of any wavelength suitable for activating the formation of the separation medium, and in some instances may have a wavelength associated with blue light in the visible spectrum. For example, the light used to activate formation of the separation medium may have a wavelength ranging from 400 nm to 500 nm, such as from 410 nm to 490 nm, including from 420 nm to 480 nm, or from 430 nm to 480 nm, or from 440 nm to 480 nm, or from 450 nm to 480 nm, or from 460 nm to 480 nm, or from 465 nm to 475 nm. In certain cases, the light used to activate formation of the separation medium has a wavelength ranging from 465 to 475 nm. In some instances, the light used to activate formation of the separation medium has a wavelength of 470 nm.

In certain embodiments, the polymeric separation medium is configured to separate constituents in a sample based on size. For example, in some cases, the polymeric separation medium includes a polymeric gel having a pore size gradient. The pore size gradient may decrease along the directional axis of the polymeric separation medium. For example, the pore size gradient may have a pore size that decreases along the directional axis of the separation medium, such that a sample traversing the polymeric separation medium encounters progressively smaller and smaller pore sizes in the polymeric separation medium. As constituents in the sample traverse the pore size gradient, the constituents in the sample may be separated based on size. For example, larger constituents in the sample may be retained in the polymeric separation medium more readily than smaller constituents, which are able to traverse greater distances through the decreasing pore size gradient.

In certain embodiments, the polymeric separation medium includes a buffer. The buffer may be any convenient buffer used for gel electrophoresis. In certain embodiments, the buffer is a Tris buffer. In certain embodiments, the separation medium includes a buffer, such as a Tris-glycine buffer. For example, the buffer may include a mixture of Tris and glycine. In some cases, the buffer includes a detergent. In certain instances, the detergent is configured to provide analytes in the sample with substantially similar charge-to-mass ratios. Analytes with substantially similar charge-to-mass ratios may facilitate the separation of the analytes into one or more bands in the separation medium based on the molecular masses of the analytes in the sample. In certain cases, the detergent is anionic detergent configured to provide analytes in the sample with a charge, such as a negative charge. For example, the detergent may be an anionic detergent, such as, but not limited to, sodium dodecyl sulfate (SDS).

While the length of the polymeric separation medium may vary, in some instances the length of the separation medium is from 0.5 mm to 200 mm, such as from 0.5 mm to 150 mm, e.g., 1 to 100 mm, or 1 mm to 90 mm, or 1 mm to 80 mm, or 1 mm to 70 mm, or 1 mm to 60 mm, or 1 mm to 50 mm, or 1 mm to 40 mm, or 1 mm to 30 mm, or 1 mm to 20 mm, or 1 mm to 10 mm, or 1 mm to 5 mm. In certain embodiments, the width of the polymeric separation medium ranges from 0.5 mm to 100 mm, such as from 0.5 mm to 90 mm, or from 0.5 mm to 80 mm, or 0.5 mm to 70 mm, or 0.5 mm to 60 mm, or 0.5 mm to 50 mm, or 1 mm to 50 mm, or 1 mm to 40 mm, or 1 mm to 30 mm, or 1 mm to 20 mm, or 1 mm to 10 mm, or 1 mm to 5 mm. In certain embodiments, the thickness of the polymeric separation medium ranges from 0.5 mm to 20 mm, of 0.5 mm to 15 mm, or 0.5 mm to 10 mm, such as from 0.5 mm to 9 mm, or 0.5 mm to 8 mm, or 0.5 mm to 7 mm, or 0.5 mm to 6 mm, or 0.5 mm to 5 mm, or 0.5 mm to 4 mm, or 0.5 mm to 3 mm, or 0.5 mm to 2 mm, or 0.5 mm to 1 mm.

In certain embodiments, the separation medium is a substantially planar separation medium. In some instances, the thickness of the separation medium is less than the length or the width of the separation medium. For example, thickness (e.g., the distance from the surface of the separation medium in contact with the support to the opposing surface of the separation medium) is less than the length or the width of the separation medium. As such, in some instances, the separation medium is disposed on the support such that the thickness of the separation medium (e.g., the smallest dimension of the separation medium) extends from the support and is substantially perpendicular to the support. In these embodiments, during an assay, the sample and/or sample components traverse the separation medium in a separation flow path with a directional axis substantially parallel to the support.

In some instances, the microfluidic devices include a sample-loading element associated with the polymeric separation medium. The sample-loading element may be configured to allow a sample to be introduced into the polymeric separation medium. The sample-loading element may be in fluid communication with the separation medium. In some instances, the sample-loading element is in fluid communication with an upstream end of the polymeric separation medium. The sample-loading element may further include a structure configured to prevent fluid from exiting the sample-loading element. For example, the sample-loading element may include one or more walls configured to substantially prevent fluid, such as the sample and/or buffer, from exiting the sample-loading element. In certain cases, the sample-loading element is configured as a well, where fluid may be placed into and retained in the well. In some instances, the sample-loading element includes one or more side walls that surround a void area. The one or more side walls may be disposed on a surface of a support and extend vertically from the surface of the support.

In certain embodiments, the sample-loading element is in fluid communication with the polymeric separation medium. In some instances, the sample-loading element is configured such that a fluid, such as a sample fluid, buffer, reagent, etc., can traverse from the sample-loading element to the polymeric separation medium. In certain cases, a portion of a wall of the sample-loading element is in fluid communication with the polymeric separation medium. In these instances, the portion of the wall of the sample-loading element that is in fluid communication with the polymeric separation medium may be configured such that a fluid, such as a sample fluid, buffer, reagent, etc., can traverse through the wall of the sample-loading element into the polymeric separation medium. In certain embodiments, the sample-loading element is composed of a polymer, such as a polymeric gel. The polymeric gel may be a gel suitable for gel electrophoresis. The polymeric gel may include, but is not limited to, a polyacrylamide gel, an agarose gel, and the like. In some instances, the sample-loading element is composed of the same polymer as the polymeric separation medium. In certain embodiments, the sample-loading element is contiguous with the polymeric separation medium. For example, the sample-loading element and the polymeric separation medium may be formed as a single unit, e.g., the polymeric separation medium may include a void area that functions as the sample-loading element as described above. In certain embodiments, the walls (e.g., the side walls) of the sample-loading element are formed by the polymeric separation medium, such as where the interior volume of the sample-loading element extends into the separation medium and is surrounded by the polymeric separation medium.

In certain embodiments, the sample-loading element has a length from 1 mm to 15 mm, such as 1 mm to 14 mm, or 1 mm to 13 mm, or 1 mm to 12 mm, or 1 mm toll mm, or 1 mm to 10 mm, or 1 mm to 9 mm, or 1 mm to 8 mm, or 1 mm to 7 mm, or 1 mm to 6 mm, or 1 mm to 5 mm, or 1 mm to 4 mm, or 1 mm to 3 mm, or 1 mm to 2 mm. In certain embodiments, the sample-loading element has a width from 1 mm to 15 mm, such as 1 mm to 14 mm, or 1 mm to 13 mm, or 1 mm to 12 mm, or 1 mm toll mm, or 1 mm to 10 mm, or 1 mm to 9 mm, or 1 mm to 8 mm, or 1 mm to 7 mm, or 1 mm to 6 mm, or 1 mm to 5 mm, or 1 mm to 4 mm, or 1 mm to 3 mm, or 1 mm to 2 mm. In some instances, the sample-loading element has a length and a width of equal dimensions, such as 2 mm×2 mm. In certain embodiments, the sample-loading element has a depth from 0.5 mm to 20 mm, of 0.5 mm to 15 mm, or 0.5 mm to 10 mm, such as from 0.5 mm to 9 mm, or 0.5 mm to 8 mm, or 0.5 mm to 7 mm, or 0.5 mm to 6 mm, or 0.5 mm to 5 mm, or 0.5 mm to 4 mm, or 0.5 mm to 3 mm, or 0.5 mm to 2 mm, or 0.5 mm to 1 mm. In certain embodiments, the sample-loading element has a volume from 1 µL to 1000 µL, such as 1 µL to 950 µL, or 1 µL to 900 µL, or 1 µL to 850 µL, or 1 µL to 800 µL, or 1 µL to 750 µL, or 1 µL to 700 µL, or 1 µL to 650 µL, or 1 µL to 600 µL, or 1 µL to 550 µL, or 1 µL to 500 µL, or 5 µL to 500 µL, or 10 µL to 500 µL, or 10 µL to 450 µL, or 10 µL to 400 µL, or 10 µL to 350 µL, or 10 µL to 300 µL, or 10 µL to 250 µL, or 10 µL to 200 µL, or 10 µL to 150 µL, or 10 µL to 100 µL.

In certain embodiments, the devices are microfluidic separation devices. A "microfluidic device" is device that is configured to control and manipulate fluids geometrically constrained to a small scale (e.g., sub-millimeter). Embodiments of the microfluidic devices include a free-standing polymeric medium, e.g., a polymeric separation medium as described herein.

In certain embodiments, the microfluidic device includes one or more electric field generators configured to generate an electric field. The electric field generator may be configured to apply an electric field to the separation medium. The electric field generators may be configured to electrokinetically transport the analytes and moieties in a sample through the various media in the microfluidic device. In certain instances, the electric field generators may be proximal to the microfluidic device, such as arranged on the microfluidic device. In some cases, the electric field generators are positioned a distance from the microfluidic device. For example, the electric field generators may be incorporated into a system for detecting an analyte, as described in more detail below. In some instances, the electric field has a voltage of 500 V or less, such as 400 V or less, or 300 V or less, or 200 V or less, or 100 V or less, such as 50V or less, including 25 V or less, e.g., 15 V or less, such as 10 V or less.

Embodiments of the support may be made of any suitable material that is compatible with the microfluidic devices and compatible with the samples, buffers, reagents, etc. used in the microfluidic devices. In some cases, the support is made of a material that is inert (e.g., does not degrade or react) with respect to the samples, buffers, reagents, etc. used in the subject microfluidic devices and methods. For instance, the support may be made of materials, such as, but not limited to, glass, quartz, polymers, elastomers, paper, combinations thereof, and the like. In certain embodiments, the solid support is substantially transparent. By "transparent" is meant that a substance allows visible light to pass through the substance. In some embodiments, a transparent solid support facilitates detection of analytes in the polymeric medium, for example analytes that include, produce, or are labeled with a detectable label, such as a fluorescent label. In some cases, the solid support is substantially opaque. By "opaque" is meant that a substance substantially blocks visible light from passing through the substance. In certain instances, an opaque solid support may facilitate the analysis of analytes that are sensitive to light, such as analytes that react or degrade in the presence of light.

In certain embodiments, the solid support is sized to accommodate the polymeric separation medium. For example the solid support may have dimensions (e.g., length and width) such that the entire polymeric separation medium is supported by the solid support. In some cases, the solid support may have dimensions (e.g., length and width) larger than the polymeric separation medium. In some instances, the solid support has dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 1 mm×1 mm or less. In some cases, the solid support has a thickness ranging from 0.5 mm to 5 mm, or 1 mm to 4 mm, of 1 mm to 3 mm, or 1 mm to 2 mm. In certain instances, the solid support has a thickness of 1 mm.

In certain embodiments, the microfluidic device has a width ranging from 10 cm to 1 mm, such as from 5 cm to 5 mm, including from 1 cm to 5 mm. In some instances, the microfluidic device has a length ranging from 100 cm to 1 mm, such as from 50 cm to 1 mm, including from 10 cm to 5 mm, or from 1 cm to 5 mm. In certain aspects, the microfluidic device has an area of 1000 $cm^2$ or less, such as 100 $cm^2$ or less, including 50 $cm^2$ or less, for example, 10 $cm^2$ or less, or 5 $cm^2$ or less, or 3 $cm^2$ or less, or 1 $cm^2$ or less, or 0.5 $cm^2$ or less, or 0.25 $cm^2$ or less, or 0.1 $cm^2$ or less.

Methods

Embodiments of the methods are directed to determining whether an analyte is present in a sample, e.g., determining the presence or absence of one or more analytes in a sample. Aspects of the method include contacting a sample with a free-standing separation medium as described above. In certain embodiments, the sample may be contacted to the polymeric separation medium such that constituents of the sample are positioned in one or more sample-loading elements associated with the separation medium. For example, the sample may be applied into the sample-loading element. In some cases, the method also includes applying an electric field to the polymeric separation medium in a manner sufficient to move at least some components of the sample from the sample-loading element into the separation medium to produce separated sample components in the separation medium.

For instance, separating the analytes in a sample may include applying an electric field configured to direct the analytes in the sample through the separation medium of the device. The electric field may be configured to facilitate the separation of the analytes in a sample based on the physical properties of the analytes. For example, the electric field may be configured to facilitate the separation of the analytes in the sample based on the molecular mass, size, charge (e.g., charge to mass ratio), isoelectric point, etc. of the analytes. In certain instances, the electric field is configured to facilitate the separation of the analytes in the sample based on the molecular mass of the analytes. In other embodiments, the electric field is configured to facilitate separation of the analytes in the sample based on the isoelectric point (pI) of the analytes.

In certain embodiments, the method includes determining whether an analyte of interest is present in a sample, e.g., determining the presence or absence of one or more analytes of interest in a sample. In some instances, the devices are configured to detect the presence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which an exact measurement of the concentration of the analyte is provided to the user.

In certain embodiments, the microfluidic devices are configured to detect the presence of one or more analytes in a sample. Samples that may be assayed with the subject microfluidic devices may vary, and include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analytes of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure or physical properties (e.g., molecular weight, size, charge, isoelectric point, etc.).

In certain embodiments, the samples of interest are biological samples, such as, but not limited to, urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like.

As described above, the samples that may be assayed in the subject methods may include one or more analytes of interest. Examples of detectable analytes include, but are not limited to: nucleic acids, e.g., double or single-stranded DNA, double or single-stranded RNA, DNA-RNA hybrids, DNA aptamers, RNA aptamers, etc.; proteins and peptides, with or without modifications, e.g., antibodies, diabodies, Fab fragments, DNA or RNA binding proteins, phosphorylated proteins (phosphoproteomics), peptide aptamers, epitopes, and the like; small molecules such as inhibitors, activators, ligands, etc.; oligo or polysaccharides; mixtures thereof; and the like.

In some embodiments, the analyte of interest can be identified so that the presence of the analyte of interest can then be detected. Analytes may be identified by any of the methods described herein. For example, an analyte specific binding member that includes a detectable label may be employed. Detectable labels include, but are not limited to, fluorescent labels, colorimetric labels, chemiluminescent labels, enzyme-linked reagents, multicolor reagents, avidin-streptavidin associated detection reagents, non-visible detectable labels (e.g., radiolabels, gold particles, magnetic labels, electrical readouts, density signals, etc.), and the like. In certain embodiments, the detectable label is a fluorescent label. Fluorescent labels are labeling moieties that are detectable by a fluorescence detector. For example, binding of a fluorescent label to an analyte of interest may allow the analyte of interest to be detected by a fluorescence detector. Examples of fluorescent labels include, but are not limited to, fluorescent molecules that fluoresce upon contact with a reagent, fluorescent molecules that fluoresce when irradiated with electromagnetic radiation (e.g., UV, visible light, x-rays, etc.), and the like.

Suitable fluorescent molecules (fluorophores) include, but are not limited to, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from Anthozoan species; combinations thereof; and the like.

As described above, detecting the analyte of interest includes contacting the analyte of interest with an analyte detection reagent (e.g., a label) configured to specifically bind to the analyte of interest (e.g., an antibody that specifically binds to the analyte of interest). For example, contacting the analyte of interest with an analyte detection reagent may include applying a solution of analyte detection reagent to the polymeric separation medium. The analyte detection reagent may be contacted to any surface of the polymeric separation medium, such as the top or one or more sides of the polymeric separation medium. In some cases, the analyte detection reagent may be moved through the polymeric separation medium such that the analyte detection reagent contacts analytes of interest immobilized within the polymeric separation medium. For instance, the analyte detection reagent may be moved through the polymeric separation medium by applying an electric field to the polymeric separation medium, applying a pressure, applying a centrifugal force, passive diffusion, and the like.

In certain embodiments, detecting the analyte of interest includes contacting the analyte of interest with a primary label that specifically binds to the analyte of interest. In certain embodiments, the method includes enhancing the detectable signal from the labeled analyte of interest. For instance, enhancing the detectable signal from the labeled analyte of interest may include contacting the primary label with a secondary label configured to specifically bind to the primary label. In certain instances, the primary label is a primary antibody that specifically binds to the analyte of interest, and the secondary label is a secondary antibody that specifically binds to the primary antibody. As such, enhancing the detectable signal from the labeled analyte of interest may include contacting the primary antibody with a secondary antibody configured to specifically bind to the primary antibody. The use of two or more detectable labels as described above may facilitate the detection of the analyte of interest by improving the signal-to-noise ratio.

In certain embodiments, the analyte detection reagent may not specifically bind to an analyte of interest. In some cases, the analyte detection reagent may be configured to produce a detectable signal from the analyte of interest without specifically binding to the analyte of interest. For example, the analyte of interest may be an enzyme (e.g., a cellular enzyme) and the analyte detection reagent may be a substrate for the enzyme. In some cases, contacting the analyte detection reagent (e.g., enzyme substrate) to the analyte of interest (e.g., enzyme) may produce a detectable signal as the substrate is converted by the enzyme.

In certain embodiments, the method includes introducing a fluid sample into a microfluidic device. Introducing the fluid sample into the microfluidic device may include directing the sample through a separation medium to produce a separated sample. In some cases, the separated sample is produced by gel electrophoresis as the sample traverses the separation medium, as described above. The separated sample may include distinct detectable bands of analytes, where each band includes one or more analytes that have substantially similar properties, such as molecular weight, size, charge (e.g., charge to mass ratio), isoelectric point, etc. depending on the type of gel electrophoresis performed.

In certain embodiments, the method includes detecting analyte fronts as they move through the separation medium. For example, the microfluidic device may be configured for a moving boundary electrophoresis (MBE) protocol. In these embodiments, the method includes detecting one or more analytes as they are separated using an MBE protocol.

In certain embodiments, the separated sample may be contacted with one or more secondary reagents. In some instances, the separated sample is contacted with the secondary reagent while the separated sample is still within the separation medium. The secondary reagent may be configured to allow additional analysis of the separated sample to be performed by the user. For instance, the one or more secondary reagents may include, but are not limited to, an affinity probe, a dye, an antibody, an enzyme, an enzyme substrate and a nucleic acid. In certain embodiments, the secondary reagent is contacted with the separated sample by diffusion. For example, the secondary reagent may be applied to a surface of the separation medium and allowed to passively diffuse through the separation medium to the separated sample constituents. In certain embodiments, the secondary reagent is contacted with the separated sample using active transport methods, such as electrokinetic transport or hydrodynamic transport.

In certain embodiments, the separated sample constituents are removed from the separation medium for subsequent analysis. In some cases, the method includes transferring one or more analytes away from the separation medium. For example, the method may include directing an analyte downstream from the separation medium for secondary analysis with a secondary analysis device such as, but is not limited to, a UV spectrometer, and IR spectrometer, a mass spectrometer, an HPLC, an affinity assay device, a second microfluidic device as described herein, and the like.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, analytes may include detectable differences in their molecular weight, size, charge (e.g., mass to charge ratio), isoelectric point, and the like. In some instances, the number of analytes is greater than 2, such as 4 or more, 6 or more, 8 or more, etc., up to 20 or more, e.g., 50 or more, including 100 or more, distinct analytes. In certain embodiments, the methods include the multiplex analysis of 2 to 100 distinct analytes, such as 4 to 50 distinct analytes, including 4 to 20 distinct analytes.

In certain embodiments, the method is configured to separate and/or detect constituents of interest in a sample, where the sample size is small. For example, the method may be configured to separate and/or detect constituents of interest in a sample, where the sample size is 1 mL or less, such as 750 µL or less, including 500 µL or less, or 250 µL or less, of 100 µL or less, or 75 µL or less, or 50 µL or less, or 40 µL or less, or 30 µL or less, or 20 µL or less, or 10 µL or less, or 5 µL or less, or 1 µL or less. In some instances, the method is configured to separate and/or detect constituents of interest in a sample, where the sample size is 20 µL or less.

In certain embodiments, the method includes concentrating, diluting, or buffer exchanging the sample prior to directing the sample through the separation medium. Concentrating the sample may include contacting the sample with a concentration medium prior to contacting the sample with the separation medium. The concentration medium may include a small pore size polymeric gel, a membrane (e.g., a size exclusion membrane), combinations thereof, and the like. Concentrating the sample prior to contacting the sample with the separation medium may facilitate an increase in the resolution between the bands of analytes in the separated sample because each separated band of analyte may disperse less as the sample traverses through the separation medium. Diluting the sample may include contacting the sample with additional buffer prior to contacting the sample with the separation medium. Buffer exchanging the sample may include contacting the sample with a buffer exchange medium prior to contacting the sample with the separation medium. The buffer exchange medium may include a buffer different from the sample buffer. The buffer exchange medium may include, but is not limited to, a molecular sieve, a porous resin, and the like.

In certain embodiments, the method is an automated method. As such, the method may include a minimum of user interaction with the microfluidic devices and systems after introducing the sample into the microfluidic device. For example, the step of directing the sample through the separation medium to produce a separated sample may be performed by the microfluidic device and system, such that the user need not manually perform these steps. In some cases, the automated method may facilitate a reduction in the total assay time. For example, embodiments of the method, including the separation and detection of analytes in a sample, may be performed in 30 min or less, such as 20 min or less, including 15 min or less, or 10 min or less, or 5 min or less, or 2 min or less, or 1 min or less.

In certain embodiments, the method includes storing the polymeric separation medium. For example, the method may include storing the polymeric separation medium by dehydrating the polymeric separation medium. The polymeric separation medium may be stored for an extended period of time, such as, but not limited to, 1 day, 2 days, 3 days, 4 days, 5 days, 6 days, 1 week, 2 weeks, 3 weeks, 1 month, 2 months, 3 months, 4 months, 5 months, 6 months or more. In some embodiments, the method further includes rehydrating the polymeric separation medium. The rehydrated polymeric separation medium may be used in any of the assay steps described herein.

Aspects of embodiments of the present disclosure further include methods of making the above polymeric separation medium. In some instances, the methods include positioning a monomeric precursor composition of the polymeric separation medium between a first surface and second surface having one or more structural features; irradiating the monomeric precursor composition with light having a wavelength sufficient (e.g., blue light) to initiate polymerization of the precursor composition so as to produce the desired composition. The method may further include removing the second surface having the one or more structural features such that the first surface (e.g., the support) carries a free-standing polymeric separation medium as described herein. In certain embodiments, the structural features on the second surface include a plurality of columns. The columns on the second surface may include shapes and sizes that correspond to the desired shapes and sizes of the interior volumes of the sample-loading elements. In embodiments that include a plurality of columns on the second surface, a free-standing polymeric separation medium may be produced that includes one or more corresponding sample-loading elements.

Systems

Aspects of certain embodiments include a system for detecting an analyte in a sample. In some instances, the system includes a microfluidic device as described herein. The system may also include a detector. In some cases, the detector is a detector configured to detect a detectable label. As described above, the detectable label may be a fluorescent label. For example, the fluorescent label can be contacted with electromagnetic radiation (e.g., visible, UV, x-ray, etc.), which excites the fluorescent label and causes the fluorescent label to emit detectable electromagnetic radiation (e.g., visible light, etc.). The emitted electromagnetic radiation may be detected with an appropriate detector to determine the presence of the analyte in a sample separated by the separation medium.

In some instances, the detector may be configured to detect emissions from a fluorescent label, as described above. In certain cases, the detector includes a photomultiplier tube (PMT), a charge-coupled device (CCD), an intensified charge-coupled device (ICCD), a complementary metal-oxide-semiconductor (CMOS) sensor, a visual colorimetric readout, a photodiode, and the like.

In certain embodiments, the system includes an environmental chamber. The environmental chamber may be configured to contain a device as disclosed herein. For instance, the environmental chamber may be configured to contain the free-standing separation medium disposed on the surface of a support. The device may be positioned inside the environmental chamber, such that device (e.g., the free-standing separation medium) is surrounded by the environment provided inside the environmental chamber. In some instances, the environmental chamber contains an environment (e.g., an assay environment) that has a higher humidity than ambient conditions. An assay environment with a higher humidity may facilitate a reduction in evaporation of liquids (e.g., buffers, etc.) from the separation medium. Embodiments of the environmental chamber may be made of any suitable material that is compatible with the devices and compatible with the samples, buffers, reagents, etc. used in the devices. In some cases, the environmental chamber is made of a material that is inert (e.g., does not degrade or react) with respect to the samples, buffers, reagents, etc. used in the subject devices and methods. For instance, the environmental chamber may be made of materials, such as, but not limited to, glass, quartz, polymers, elastomers, paper, combinations thereof, and the like. In certain embodiments, the environmental chamber includes one or more portions that are substantially transparent. In some embodiments, an environmental chamber with one or more transparent areas facilitates detection of analytes in the polymeric separation medium, for example analytes that include, produce, or are labeled with a detectable label, such as a fluorescent label.

Systems of the present disclosure may include various other components as desired. For example, the systems may include fluid handling components, such as microfluidic fluid handling components. The fluid handling components may be configured to direct one or more fluids to and/or from the microfluidic device. In some instances, the fluid handling components are configured to direct fluids, such as, but not limited to, sample solutions, buffers (e.g., release buffers, wash buffers, electrophoresis buffers, etc.), and the like. In certain embodiments, the microfluidic fluid handling components are configured to deliver a fluid to the separation medium (or sample-loading element) of the microfluidic device, such that the fluid contacts the separation medium (or sample-loading element). The fluid handling components may include microfluidic pumps. In some cases, the microfluidic pumps are configured for pressure-driven microfluidic handling and routing of fluids to and/or from the microfluidic devices and systems disclosed herein. In certain instances, the microfluidic fluid handling components are configured to deliver small volumes of fluid, such as 1 mL or less, such as 500 µL or less, including 100 µL or less, for example 50 µL or less, or 25 µL or less, or 10 µL or less, or 5 µL or less, or 1 µL or less.

In certain embodiments, the systems include one or more electric field generators. An electric field generator may be configured to apply an electric field to various regions of the microfluidic device. The system may be configured to apply an electric field such that the sample is electrokinetically transported through the microfluidic device. For example, the electric field generator may be configured to apply an electric field to the separation medium. In some cases, the applied electric field may be aligned with the directional axis of the separation flow path of the separation medium. As such, the applied electric field may be configured to electrokinetically transport the analytes and moieties in a sample through the separation medium. In some cases, the applied electric field is configured to electrokinetically transport selected analytes that have been separated by the separation medium. Selected analytes that have been separated by the separation medium may be transported to a second medium (e.g., a blotting medium) or a collection reservoir for subsequent analysis by applying an appropriate electric field to the separation medium along a desired directional axis. In some cases, the directional axis is orthogonal to the directional axis of the separation medium used during separation of the analytes in the sample. In some instances, the electric field generators are configured to apply an electric field with a strength ranging from 10 V/cm to 1000 V/cm, such as from 100 V/cm to 800 V/cm, including from 200 V/cm to 600 V/cm.

In certain embodiments, the electric field generators include voltage shaping components. In some cases, the voltage shaping components are configured to control the strength of the applied electric field, such that the applied electric field strength is substantially uniform across the separation medium. The voltage shaping components may facilitate an increase in the resolution of the analytes in the sample. For instance, the voltage shaping components may facilitate a reduction in non-uniform movement of the sample through the separation medium. In addition, the voltage shaping components may facilitate a minimization in the dispersion of the bands of analytes as the analytes traverses the separation medium.

In certain embodiments, the subject system is a biochip (e.g., a biosensor chip). By "biochip" or "biosensor chip" is meant a microfluidic system that includes a support surface which displays two or more distinct microfluidic devices on the support surface. In certain embodiments, the microfluidic system includes a support surface with an array of microfluidic devices.

An "array" includes any two-dimensional or substantially two-dimensional (as well as a three-dimensional) arrangement of addressable regions, e.g., spatially addressable regions. An array is "addressable" when it has multiple devices positioned at particular predetermined locations (e.g., "addresses") on the array. Array features (e.g., devices) may be separated by intervening spaces. Any given support may carry one, two, four or more arrays disposed on a front surface of the support. Depending upon the use, any or all of the arrays may be the same or different from one another and each may contain multiple distinct microfluidic devices. An array may contain one or more, including two or more, four or more, 8 or more, 10 or more, 50 or more, or 75 or more, or 100 or more microfluidic devices. In certain embodiments, the microfluidic devices can be arranged into an array with an area of less than 150 cm$^2$, or less than 100 cm$^2$, e.g., less than 75 cm$^2$, including less than 50 cm$^2$, less than 20 cm$^2$, such as less than 10 cm$^2$, or even smaller. For example, microfluidic devices may have dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 1 mm×1 mm or less.

Arrays of microfluidic devices may be arranged for the multiplex analysis of samples. For example, two or more microfluidic devices may be disposed on a support, such as 5 or more, or 10 or more, or 20 or more, or 30 or more, or 40 or more, or 50 or more, or 60 or more, or 70 or more, or 80 or more, or 90 or more, or 100 or more, or 125 or more, or 150 or more, or 175 or more, or 200 or more, or 225 or more, or 250 or more, or 275 or more, or 300 or more, or 325 or more, or 350 or more, or 375 or more, or 400 or more, or 425 or more, or 450 or more, or 475 or more, or 500 or more microfluidic devices on a support. In some instances, 75 to 100, such as 96 microfluidic devices are provided on a support. In some instances, 375 to 400, such as 384 microfluidic devices are provided on a support. In some embodiments, two or more microfluidic devices are arranged in series, such that the separation media of the microfluidic devices are arranged in series. In certain embodiments, two or more microfluidic devices are arranged in series, such as 3 or more, or 4 or more, or 5 or more, or 6 or more, or 7 or more, or 8 or more, or 9 or more, or 10 or more, or 11 or more, or 12 or more, or 13 or more, or 14 or more, or 15 or more, or 16 or more, or 17 or more, or 18 or more, or 19 or more, or 20 or more, or 21 or more, or 22 or more, or 23 or more, or 24 or more, or 25 or more. In some instances, 12 microfluidic devices are arranged in series. In some instances, 24 microfluidic devices are arranged in series.

In certain embodiments, the separation medium is composed of a polymer, such as a polymeric gel, as described above. The polymeric gel may be a gel suitable for gel electrophoresis. The polymeric gel may include, but is not limited to, a polyacrylamide gel, an agarose gel, and the like. In some instances, where two or more separation media are arranged in series, the separation media are composed of the same polymer. In certain embodiments, the series arrangement of separation media is a contiguous separation medium. For example, the series arrangement of separation media may be formed as a single unit. In these embodiments, a single separation medium may be configured to contain two or more separation regions, where an individual assay may be performed in each separation region. As described above, each separation medium (e.g., separation region) may be associated with a sample-loading element, such as a well or void area that functions as the sample-loading element as described above. In embodiments that include a series arrangement of separation regions each separation region may be associated with a sample-loading element. For example, if the series arrangement of separation regions is formed from a contiguous separation medium, each separation region may be associated with a sample-loading element, such that two or more sample-loading elements are provided in the contiguous separation medium.

In certain embodiments, two or more microfluidic devices are arranged in parallel. In embodiments where two or more microfluidic devices are arranged in parallel, two or more samples may be analyzed at substantially the same time. In certain embodiments, two or more microfluidic devices (or two or more series arrangements of microfluidic devices as described above) are arranged in parallel, such as 3 or more, or 4 or more, or 5 or more, or 6 or more, or 7 or more, or 8 or more, or 9 or more, or 10 or more, or 11 or more, or 12 or more, or 13 or more, or 14 or more, or 15 or more, or 16 or more, or 17 or more, or 18 or more, or 19 or more, or 20 or more, or 21 or more, or 22 or more, or 23 or more, or 24 or more, or 25 or more. In some instances, 8 microfluidic devices (or two or more series arrangements of microfluidic devices as described above) are arranged in parallel. In some instances, 16 microfluidic devices (or two or more series arrangements of microfluidic devices as described above) are arranged in parallel.

In certain instances, two or more separation media are arranged in series (as described above) and two or more of these series arrangements of separation media are arranged in parallel as described above. For example, 12 microfluidic devices may be arranged in series and 8 of these series arrangements of microfluidic devices may be arranged in parallel, for an array of 96 microfluidic devices. In some instances, 24 microfluidic devices are arranged in series and 16 of these series arrangements of microfluidic devices may be arranged in parallel, for an array of 384 microfluidic devices.

In certain embodiments, two or more sample-loading elements are arranged in an array. In some instances, the sample-loading elements are arranged such that they are spaced apart from adjacent sample-loading elements. For example, the distance from a center of a sample-loading element to an adjacent sample-loading element may be 10 mm or less. In some cases, the distance from a center of a sample-loading element to an adjacent sample-loading element is 9 mm. In some cases, the distance from a center of a sample-loading element to an adjacent sample-loading element is 4.5 mm. In certain embodiments, the array of sample-loading elements are arranged such that the spacing between sample-loading elements corresponds to the arrangement of wells on a standard microtiter plate, such as a 96 well microtiter plate, or a 384 well microtiter plate.

Aspects of the systems include that the microfluidic devices may be configured to consume a minimum amount of sample while still producing detectable results. For example, the system may be configured to use a sample volume of 100 µL or less, such as 75 µL or less, including 50 µL or less, or 25 µL or less, or 10 µL or less, for example, 5 µL or less, 2 µL or less, or 1 µL or less while still producing detectable results. In certain embodiments, the system is configured to have a detection sensitivity of 1 nM or less, such as 500 pM or less, including 100 pM or less, for instance, 1 pM or less, or 500 fM or less, or 250 fM or less, such as 100 fM or less, including 50 fM or less, or 25 fM or less, or 10 fM or less. In some instances, the system is configured to be able to detect analytes at a concentration of 1 µg/mL or less, such as 500 ng/mL or less, including 100 ng/mL or less, for example, 10 mg/mL or less, or 5 ng/mL or less, such as 1 ng/mL or less, or 0.1 ng/mL or less, or 0.01 ng/mL or less, including 1 µg/mL or less. In certain embodiments, the system has a dynamic range from $10^{-18}$ M to 10 M, such as from $10^{-15}$ M to $10^{-3}$ M, including from $10^{-12}$ M to $10^{-6}$ M.

In certain embodiments, the microfluidic devices are operated at a temperature ranging from 1° C. to 100° C., such as from 5° C. to 75° C., including from 10° C. to 50° C., or from 20° C. to 40° C. In some instances, the microfluidic devices are operated at a temperature ranging from 35° C. to 40° C.

Utility

In certain embodiments, the devices, systems and methods of the present disclosure find use in high-throughput electrophoretic protein separations. For example, the subject devices, systems and methods find use in applications where determination of the presence or absence, and/or quantification of one or more analytes (e.g., proteins) in a sample is desired. For example, the subject devices, systems and methods find use in the separation and detection of proteins, peptides, nucleic acids, and the like. In some cases, the subject devices, systems and methods find use in the separation and detection of proteins.

The subject devices, systems and methods find use in a variety of different applications where determination of the presence or absence, and/or quantification of one or more analytes in a sample is desired. In certain embodiments, the methods are directed to the detection of nucleic acids, proteins, or other biomolecules in a sample. The methods may include the detection of a set of biomarkers, e.g., two or more distinct protein biomarkers, in a sample. For example, the methods may be used in the rapid, clinical detection of two or more disease biomarkers in a biological sample, e.g., as may be employed in the diagnosis of a disease condition in a subject, in the ongoing management or treatment of a disease condition in a subject, etc. In addition, the subject devices, systems and methods may find use in protocols for the detection of an analyte in a sample, such as, but not limited to, Western blotting, Southern blotting, Northern blotting, Eastern, Far-Western blotting, Southwestern blotting, and the like.

In certain embodiments, the subject devices, systems and methods find use in detecting biomarkers. In some cases, the subject devices, systems and methods may be used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject devices, systems and methods. Furthermore, the early detection of biomarkers associated with diseases is facilitated by the high sensitivity of the subject devices and systems, as described above. Due to the capability of detecting multiple biomarkers on a single chip, combined with sensitivity, scalability, and ease of use, the presently disclosed microfluidic devices, systems and methods finds use in portable and point-of-care or near-patient molecular diagnostics.

In certain embodiments, the subject devices, systems and methods find use in detecting biomarkers for a disease or disease state. In some cases, the disease is a cellular proliferative disease, such as but not limited to, a cancer, a tumor, a papilloma, a sarcoma, or a carcinoma, and the like. In certain instances, the subject devices, systems and methods find use in detecting biomarkers for the characterization of cell signaling pathways and intracellular communication for drug discovery and vaccine development. For example, the subject devices, systems and methods find use in detecting the presence of a disease, such as a cellular proliferative disease, such as a cancer, tumor, papilloma, sarcoma, carcinoma, or the like. In certain instances, particular biomarkers of interest for detecting cancer or indicators of a cellular proliferative disease include, but are not limited to the following: prostate specific antigen (PSA), which is a prostate cancer biomarker; C-reactive protein, which is an indicator of inflammation; transcription factors, such as p53, which facilitates cell cycle and apoptosis control; polyamine concentration, which is an indicator of actinic keratosis and squamous cell carcinoma; proliferating cell nuclear antigen (PCNA), which is a cell cycle related protein expressed in the nucleus of cells that are in the proliferative growth phase; growth factors, such as IGF-I; growth factor binding proteins, such as IGFBP-3; micro-RNAs, which are single-stranded RNA molecules of about 21-23 nucleotides in length that regulate gene expression; carbohydrate antigen CA19.9, which is a pancreatic and colon cancer biomarker; cyclin-dependent kinases; epithelial growth factor (EGF); vascular endothelial growth factor (VEGF); protein tyrosine kinases; over-expression of estrogen receptor (ER) and progesterone receptor (PR); and the like. For example, the subject devices, systems and methods may be used to detect and/or quantify the amount of endogenous prostate specific antigen (PSA) in diseased, healthy and benign samples.

In certain embodiments, the subject devices, systems and methods find use in detecting biomarkers for an infectious disease or disease state. In some cases, the biomarkers can be molecular biomarkers, such as but not limited to proteins, nucleic acids, carbohydrates, small molecules, and the like. For example, the subject devices, systems and methods may be used to monitor HIV viral load and patient CD4 count for HIV/AIDS diagnosis and/or therapy monitoring by functionalizing the sensor surface with antibodies to HIV capsid protein p24, glycoprotiens 120 and 41, CD4+ cells, and the like. Particular diseases or disease states that may be detected by the subject devices, systems and methods include, but are not limited to, bacterial infections, viral infections, increased or decreased gene expression, chromosomal abnormalities (e.g. deletions or insertions), and the like. For example, the subject devices, systems and methods can be used to detect gastrointestinal infections, such as but not limited to, aseptic meningitis, botulism, cholera, *E. coli* infection, hand-foot-mouth disease, helicobacter infection, hemorrhagic conjunctivitis, herpangina, myocaditis, paratyphoid fever, polio, shigellosis, typhoid fever, vibrio septicemia, viral diarrhea, etc. In addition, the subject devices, systems and methods can be used to detect respiratory infections, such as but not limited to, adenovirus infection, atypical pneumonia, avian influenza, swine influenza, bubonic plague, diphtheria, influenza, measles, meningococcal meningitis, mumps, parainfluenza, pertussis (i.e., whooping cough), pneumonia, pneumonic plague, respiratory syncytial virus infection, *rubella*, scarlet fever, septicemic plague, severe acute respiratory syndrome (SARS), tuberculosis, etc. In addition, the subject devices, systems and methods can be used to detect neurological diseases, such as but not limited to, Creutzfeldt-Jakob disease, bovine spongiform encephalopathy (i.e., mad cow disease), Parkinson's disease, Alzheimer's disease, rabies, etc. In addition, the subject devices, systems and methods can be used to detect urogenital diseases, such as but not limited to, AIDS, chancroid, *Chlamydia*, condyloma accuminata, genital herpes, gonorrhea, lymphogranuloma venereum, non-gonococcal urethritis, syphilis, etc. In addition, the subject devices, systems and methods can be used to detect viral hepatitis diseases, such as but not limited to, hepatitis A, hepatitis B, hepatitis C, hepatitis D, hepatitis E, etc. In addition, the subject devices, systems and methods can be used to detect hemorrhagic fever diseases, such as but not limited to, Ebola hemorrhagic fever, hemorrhagic fever with renal syndrome (HFRS), Lassa hemorrhagic fever, Marburg hemorrhagic fever, etc. In addition, the subject devices, systems and methods can be used to detect zoonosis diseases, such as but not limited to, anthrax, avian influenza, brucellosis, Creutzfeldt-Jakob disease, bovine spongiform encephalopathy (i.e., mad cow disease), enterovirulent *E. coli* infection, Japanese encephalitis, leptospirosis, Q fever, rabies, sever acute respiratory syndrome (SARS), etc. In addition, the subject devices, systems and methods can be used to detect arbovirus infections, such as but not limited to, Dengue hemorrhagic fever, Japanese encephalitis, tick-borne encephalitis, West Nile fever, Yellow fever, etc. In addition, the subject devices, systems and methods can be used to detect antibiotics-resistance infections, such as but not limited to, *Acinetobacter baumannii, Candida albicans, Enterococci* sp., *Klebsiella pneumoniae, Pseudomonas aeruginosa, Staphylococcus aureus*, etc. In addition, the subject devices, systems and methods can be used to detect vector-borne infections, such as but not limited to, cat scratch disease, endemic typhus, epidemic typhus, human ehrlichosis, Japanese spotted fever, louse-borne relapsing fever, Lyme disease, malaria, trench fever, Tsutsugamushi disease, etc. Similarly, the subject devices, systems and methods can be used to detect cardiovascular diseases, central nervous diseases, kidney failures, diabetes, autoimmune diseases, and many other diseases.

The subject device, systems and methods find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

The subject devices, systems and methods also find use in validation assays. For example, validation assays may be used to validate or confirm that a potential disease biomarker is a reliable indicator of the presence or absence of a disease across a variety of individuals. The short assay times for the subject devices, systems and methods may facilitate an increase in the throughput for screening a plurality of samples in a minimum amount of time.

In some embodiments, the devices, systems and methods of the present disclosure facilitate sample extraction or downstream processing of the separated sample, for example by subsequent immunological blotting, mass spectrometry, and the like.

In some instances, the subject devices, systems and methods can be used without requiring a laboratory setting for implementation. In comparison to the equivalent analytic research laboratory equipment, the subject devices and systems provide comparable analytic sensitivity in a portable, hand-held system. In some cases, the weight and operating cost are less than the typical stationary laboratory equipment. The subject systems and devices may be integrated into a single apparatus, such that all the steps of the assay, including separation, transfer, labeling and detecting of an analyte of interest, may be performed by a single apparatus. For example, in some instances, there are no separate apparatuses for separation, transfer, labeling and detecting of an analyte of interest. In addition, the subject systems and devices can be utilized in a home setting for over-the-counter home testing by a person without medical training to detect one or more analytes in samples. The subject systems and devices may also be utilized in a clinical setting, e.g., at the bedside, for rapid diagnosis or in a setting where stationary research laboratory equipment is not provided due to cost or other reasons.

Kits

Aspects of the present disclosure additionally include kits that have a device as described in detail herein. In some instances, the kits include a device as described herein, such as a device that includes a free-standing polymeric separation medium. In certain embodiments, the kit may include a packaging configured to contain the device. The packaging may be a sealed packaging, such as a sterile sealed packaging. By "sterile" is meant that there are substantially no microbes (such as fungi, bacteria, viruses, spore forms, etc.). In some instances, the packaging may be configured to be sealed, e.g., a water vapor-resistant packaging, optionally under an air-tight and/or vacuum seal.

The kits may further include a buffer. For instance, the kit may include a buffer, such as an electrophoretic buffer, a sample buffer, and the like. In certain cases, the buffer is an electrophoresis buffer, such as, but not limited to, a Tris buffer, a Tris-glycine, and the like. In some instances, the buffer includes a detergent (such as sodium dodecyl sulfate, SDS).

The kits may further include additional reagents, such as but not limited to, release reagents, denaturing reagents, refolding reagents, detergents, detectable labels (e.g., fluorescent labels, colorimetric labels, chemiluminescent labels, multicolor reagents, enzyme-linked reagents, detection reagents (e.g., avidin-streptavidin associated detection reagents), e.g., in the form of at least one if not more analyte detection reagents (such as first and second analyte detection reagents), calibration standards, radiolabels, gold particles, magnetic labels, etc.), and the like.

In certain embodiments, the kit may include an analyte detection reagent, such as a detectable label, as described herein. The detectable label may be associated with a member of a specific binding pair. Suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. In certain embodiments, the member of the specific binding pair includes an antibody. The antibody may specifically bind to an analyte of interest in the separated sample bound to the separation medium. For example, the detectable label may include a labeled antibody (e.g., a fluorescently labeled antibody) that specifically binds to the analyte of interest.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-Ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Example 1

Open-Channel Microfluidics: Free-Standing Hydrogel Microarrays for Protein Electrophoresis Summary Experiments were performed using free-standing polyacrylamide gels, which served as both an open-microchannel and a sieving matrix for protein sizing. The free-standing polyacrylamide gels allowed for downstream sample access for immunoblotting after microfluidic protein separations were performed. For the purposes of multiplexing, the size of the free-standing gel was minimized to a single channel, and one or more channels may be provided on a support. In some instances, moving boundary electrophoresis (MBE) protein separations were performed.

The free-standing polyacrylamide gels where not enclosed in a microchannel, which facilitated the use of the gels with automated robotic controllers and downstream processing (e.g., sample spotters, immunological detection, mass spectroscopy, etc.). The accessibility of the free-standing polyacrylamide gels facilitated massively parallelized proteomics for bioanalytical technology.

Figure 1B:
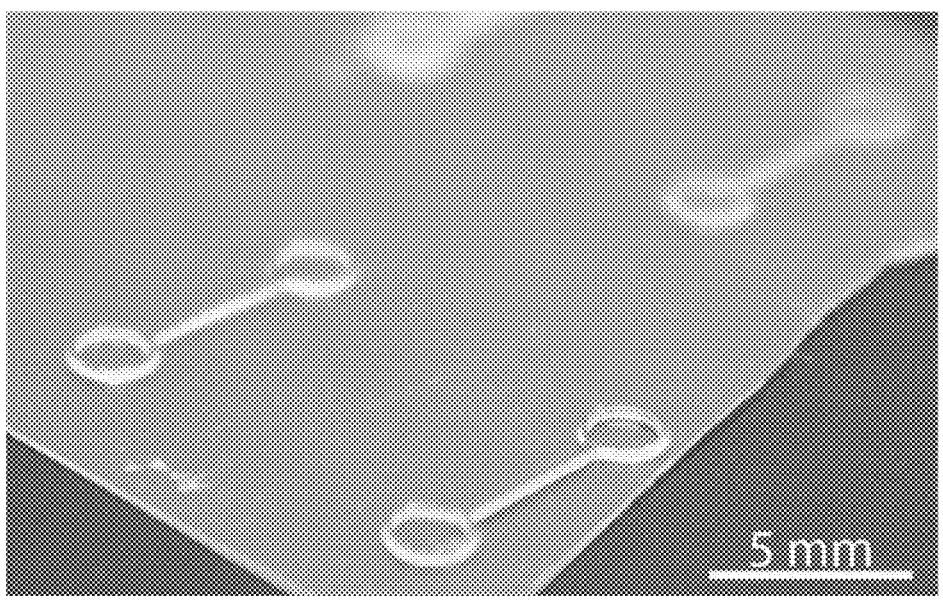

In certain embodiments, the presently disclosed device includes an open-channel format for protein electrophoresis (FIGS. 1A and 1B). A photo-patterning technique was used to produce free-standing polyacrylamide gel microchannels. A protein separation was performed in a single free-standing microchannel by moving boundary electrophoresis (MBE). In MBE, the moving boundary of an analyte was analyzed, as opposed to discrete zones, thus eliminating the need for an injection channel. Polyacrylamide gel MBE facilitated rapid protein separations in short single channels. The MBE format allowed separations to be performed on a small device and with low power consumption, which facilitated multiplexed array protocols.

Materials and Methods

Materials

Solutions of 30% (29:1) acrylamide/bis-acrylamide, 3-(trimethoxysilyl)-propyl methacrylate (98%), glacial acetic acid, methanol and glass coverslips (Sigma Aldrich, St. Louis, Mo.) were used. Photoinitiator 2,2-azobis[2-methyl-N-(2-hydroxyethyl) propionamide] (VA-086) (Wako Chemical, Richmond, Va.) was used. Alexa Fluor 488 conjugated Trypsin Inhibitor (TI), Ovalubmin (OVA), and Bovine Serum Albumin (BSA) (Sigma) were used. Tris-glycine (10×) native electrophoresis buffer (Bio-Rad Laboratories, Hercules, Calif.) was used.

Coverslip Functionalization

A glass coverslip was cleaned in a 1M NaOH solution for 30 minutes and then washed with deionized (DI) water and dried with nitrogen. A 20 μL drop of 2:3:5 (v/v/v) mixture of 3-(trimethoxysilyl)-propyl methacrylate, glacial acetic acid and DI water was sandwiched between a petri dish and a cleaned coverslip. The petri dish was sealed and placed in a refrigerator at 4° C. overnight. Afterwards the coverslip was rinsed with methanol and DI water and stored dry until it was used.

Free-Standing Gel Fabrication

Figure 2:
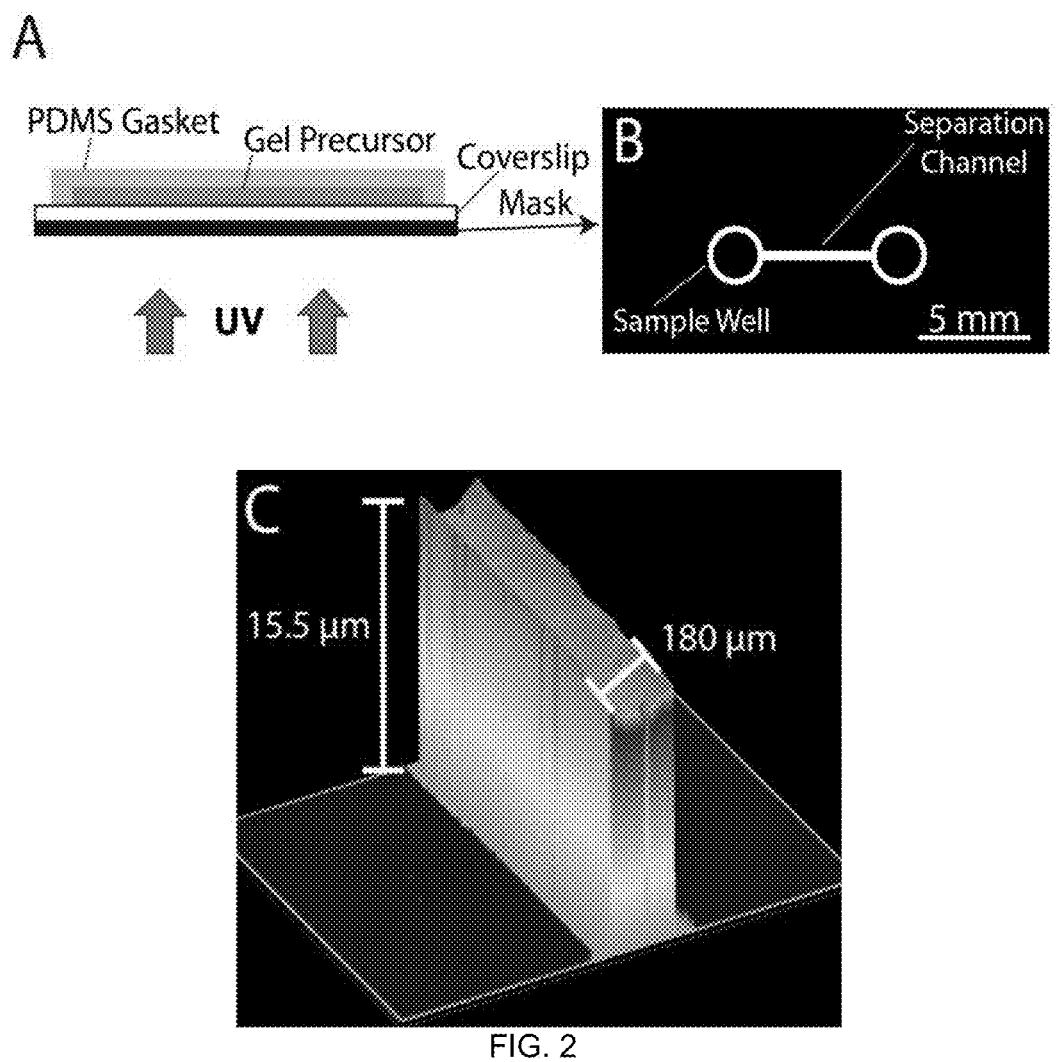
FIG. 2A shows a drawing of the fabrication of free-standing polyacrylamide gel microchannels using a mask based photolithography process, according to embodiments of the present disclosure. A reservoir of gel precursor was contained above a methacrylate functionalized coverslip. The desired micropattern was defined by a photo-mask, which determined the portions of the reservoir that were polymerized by a UV light source.
FIG. 2B shows a drawing of a single channel connecting two fluid reservoirs, according to embodiments of the present disclosure.
FIG. 2C shows an optical profilometry image showing a well-defined free-standing hydrogel with dimensions and uniformity appropriate for performing electrokinetic protein separations, according to embodiments of the present disclosure.

Gel precursor solution included a 10% (w/v) acrylamide concentration with a bis-acrylamide crosslinker ratio of 3% (w/w), and 1% (w/v) VA-086 dissolved in DI water. After degassing, the precursor solution was placed in a polydimethylsiloxane gasket atop a glass coverslip that was functionalized with methacrylate (FIG. 2A). A Blak-Ray® UV lamp at 10 mW/cm² was exposed through a Mylar photomask (FIG. 2B) on the back side of the coverslip for 5 minutes. After polymerization, the gasket was removed and excess precursor was washed away leaving only the free-standing gel microstructure on the coverslip. Fluid reservoirs were fabricated using circular rings of gel. The fluid reservoirs had the capacity to hold 2 μL of sample delivered with a pipette.

Optical profilometry was performed to confirm a high level of controllability in the free-standing structure with a channel cross section of 180 μm wide by 15.5 μm tall in its hydrated state (FIG. 2C). The gels were dehydrated for storage. The gels could be rehydrated in an aqueous buffer and ready for use within minutes.

Experimental

Environmental Chamber

Figure 17:
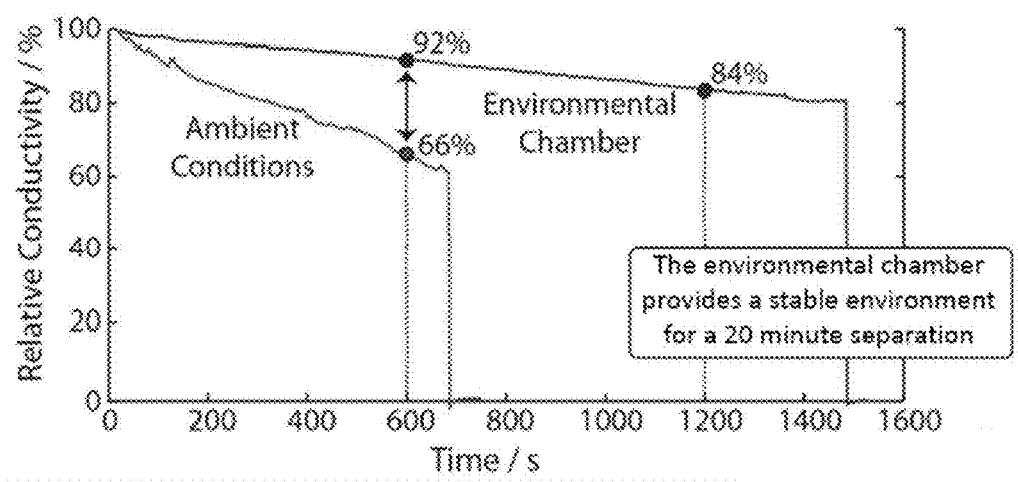
FIG. 17 shows a graph of relative conductivity vs. time (sec) for a free-standing polyacrylamide microchannel array in ambient conditions and in an environmental chamber, according to embodiments of the present disclosure.

In ambient conditions rapid evaporation was observed that resulted in fluctuations in electrical current over the course of a separation. To minimize evaporation, an environmental chamber was used, which included an inverted petri dish and a moist KIMWIPE®. Using this technique a stable electrical current was established. The environmental chamber provided a stable environment during the separation assay (see FIG. 17). FIG. 17 shows a graph of relative conductivity vs. time (sec) for a free-standing polyacrylamide microchannel array in ambient conditions and in an environmental chamber.

Testing Procedure

Free-standing gels were rehydrated in 1× tris/glycine for 5 minutes. After gel hydration the excess buffer was removed from the gel using a KIMWIPE®. A sample was pipetted into the sample well and a run buffer was pipetted into the opposite, sample wash well. Platinum electrodes were aligned and inserted from above into the two wells and electrophoresis was immediately initiated by a Caliper high voltage power supply.

Protein fronts were visualized using an inverted epifluorescence microscope (Olympus IX-70) equipped with a 100V mercury arc lamp, a 10× objective, and a Peltier-cooled charge-coupled device (CCD) camera (CoolSNAP HQ2, Roper Scientific, Trenton, N.J.). Images were recorded using MetaMorph® acquisition software and post-processing was done in ImageJ (NIH) and MATLAB®.

Separation Efficiency

The ability to resolve two analytes was quantified through 'separation resolution' (SR, the mean distance between neighboring peaks normalized by the average peak width). A SR>1 indicates a separation where the analytes are sufficiently resolved. The "critical separation length" or "critical SR" was the migration distance that corresponded to a SR>1. A lower critical separation length indicated that the separation assay may be performed in a shorter channel length.

Results

Figure 3:
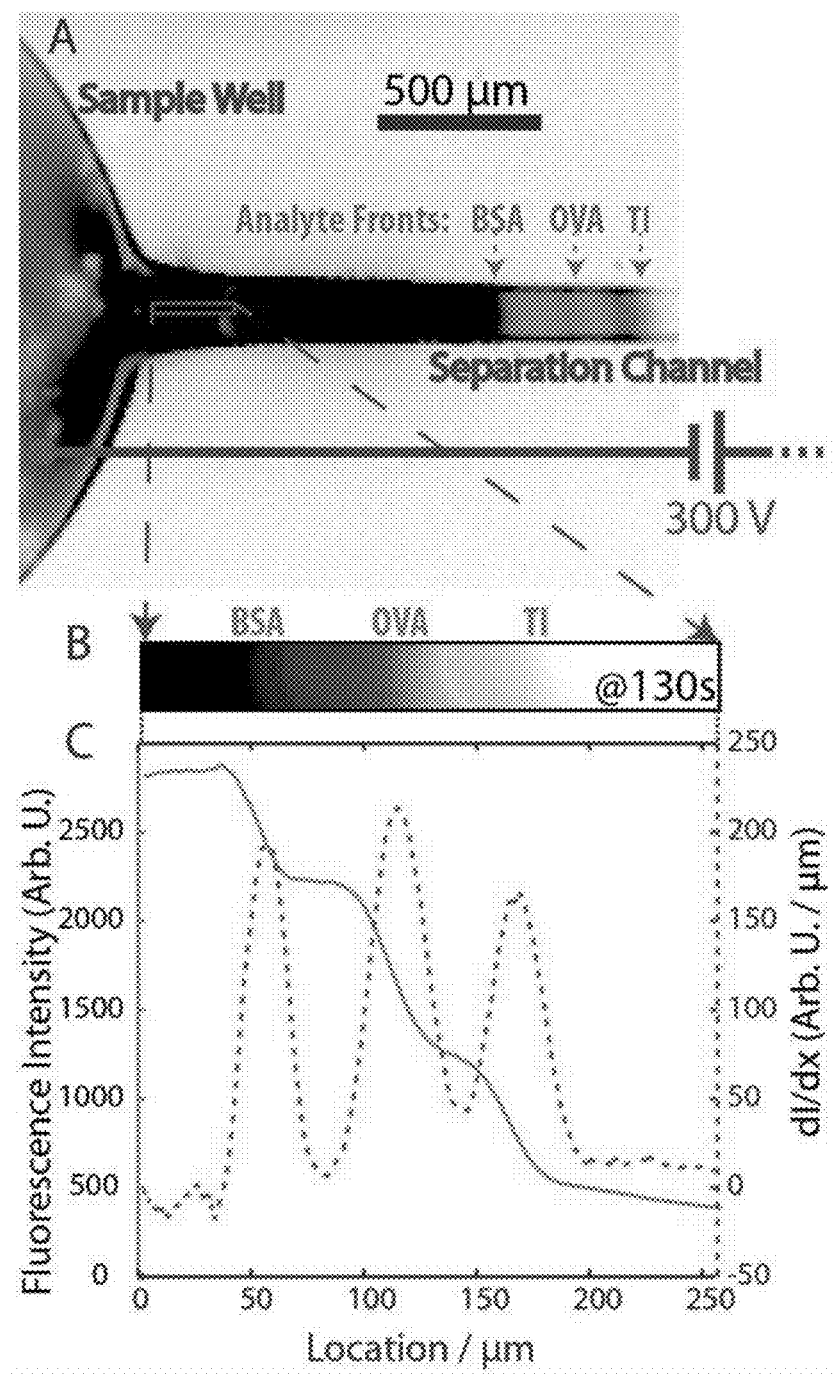
FIG. 3A shows an image of a free-standing 10% (w/v) acrylamide gel used as both the microchannel and sieving matrix for a native MBE separation, according to embodiments of the present disclosure. A 250 nM fluorescently labeled protein ladder that included Trypsin Inhibitor (TI), Ovalbumin (OVA) and Bovine Serum Albumin (BSA) was photographed in an epi-fluorescence image.
FIG. 3B shows an image of the first 250 μm of the separation channel at 130 s, which shows the separated proteins.
FIG. 3C shows a graph of the corresponding intensity profile, with the derivative of the front dI/dx overlaid (dashed lines).
FIG. 3D shows a graph of current (μA vs. time (min)), which indicates that the environmental chamber prevented significant current reduction.

A protein separation was performed in the free-standing polyacrylamide gel format and is shown in FIG. 3. A fluorescently labeled sample of 250 nm BSA, 250 nm OVA, and 250 nm TI in 1× tris/glycine was baseline resolved in 2 minutes and in the first 250 μm of migration. In FIG. 3A the protein moving boundaries were clearly visible several millimeters along the separation channel. FIG. 3B shows an enlargement of the first 250 µm of migration at 130 seconds into the separation. The image was false colored such that the TI, OVA, and BSA fronts can be clearly distinguished. The corresponding fluorescence intensity plot is shown in FIG. 3C and is overlaid with the derivative of the intensity over location (dI/dx) (dashed line). In the dI/dx plot the distinct proteins can be clearly identified. FIG. 3D shows a graph of current (µA vs. time (min)), which indicated that the environmental chamber prevented significant current reduction.

Figure 4:
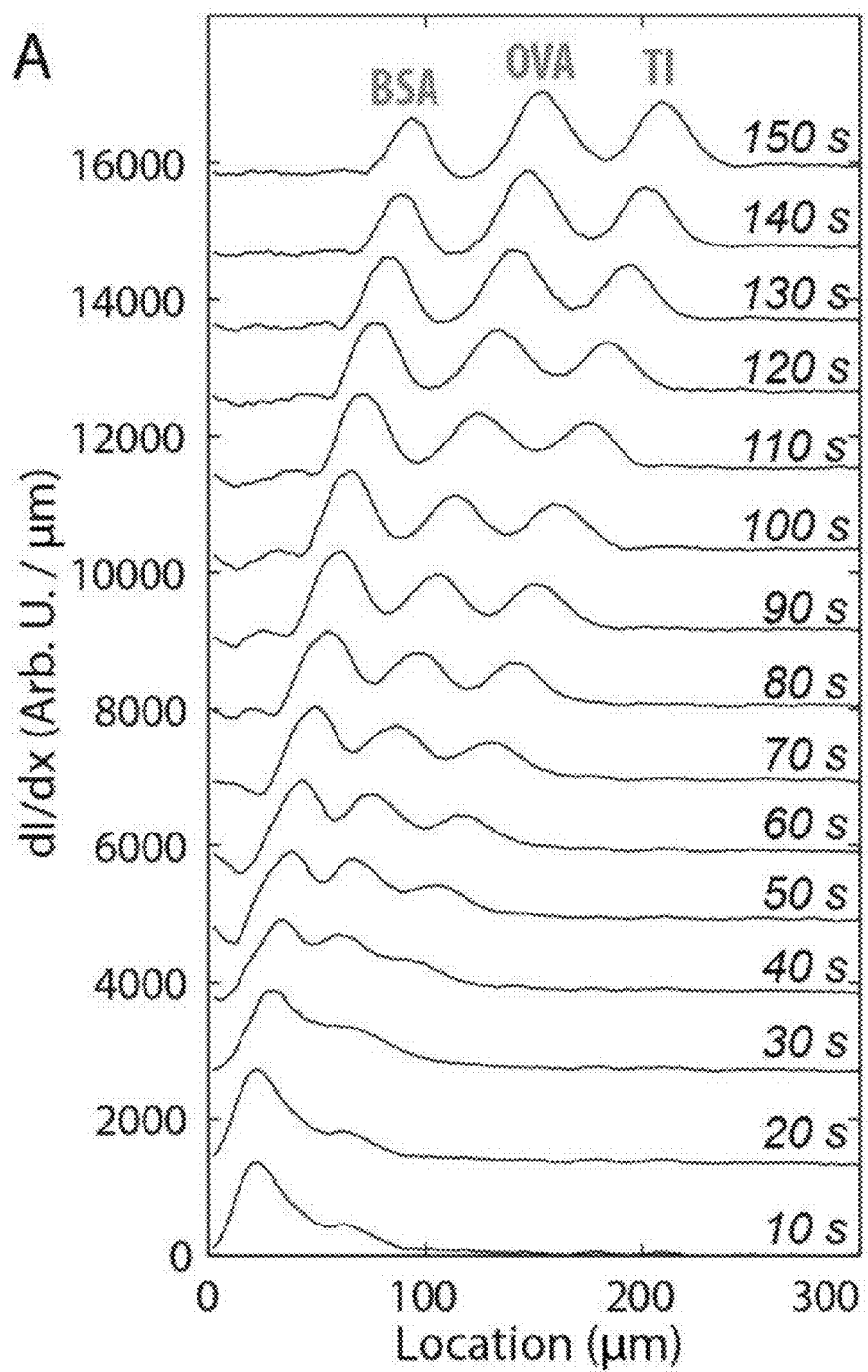
FIG. 4A shows a graph of a moving boundary electrophoresis (MBE) free-standing gel separation of a three protein ladder, which was completed in 50 s and in the first 150 μm, according to embodiments of the present disclosure. Graphs of dI/dx vs. location (mm) are shown at various time points, which show the protein migration over time.
FIG. 4B shows a graph of separation resolution (SR) vs. time (sec) for each protein separation from the experiment shown in FIGS. 3A-3D, according to embodiments of the present disclosure.

To visualize the separation in location and time, dI/dx was plotted at 10 second intervals along the first 250 µm of migration, as shown in FIG. 4A. As the separation progressed in time and location the resolution between the proteins increased. An automated Matlab Gaussian curve fitting program was used to determine the mean location and the dispersion of the protein species. The separation resolution was plotted as a function of time, as shown in FIG. 4B. All three separations passed the critical SR in less than 50 seconds.

Example 2

Photopatterned Free-Standing Polyacrylamide Gels for Microfluidic Protein Electrophoresis Summary Free-standing polyacrylamide gel (fsPAG) microstructures included a sample reservoir and contiguous separation gel. No enclosed microfluidic channels were used. The fsPAG structures (120 µm tall) were directly photopatterned on top of and covalently attached to a planar polymer or glass surface. The fsPAG architecture was configured to minimize injection dispersion for rapid (<1 min) and short (1 mm) protein separations. A polyacrylamide gel with a spatial pore-size distribution was fabricated and used to demonstrate the resulting enhancement in separation performance over a uniform gel. An array of 96 concurrent fsPAGE assays was performed in a 10 min run time driven by one electrode pair. The fsPAG array layout corresponded to that of a 96-well plate to facilitate integration of the planar free standing gel array with multi-channel pipettes while remaining compatible with conventional slab-gel PAGE reagents, such as staining for label free protein detection.

Using the fsPAG structures, experiments were performed to characterize protein fsPAGE performance, including: (i) injection mode and resultant injection dispersion, (ii) PA gel pore-size distribution along the fsPAG separation lane and the effect on separation, and (iii) concurrent operation of 96 fsPAG assays through a single electrode pair and the variation of migration across the array.

Experimental

Materials and Methods
Reagents

Solutions of 30% (w/v) (29:1) acrylamide/bis-acrylamide, glacial acetic acid, glycerol, ethanol, methanol, SYPRO Ruby protein gel stain, Brij L23, and Triton X-100 were used from Sigma Aldrich (St. Louis, Mo.). Photoinitiator 2,2-azobis[2-methyl-N-(2-hydroxyethyl) propionamide] (VA-086) was used from Wako Chemical (Richmond, Va.). Molecular biology grade (DNase-, RNase-, and Protease-free) water was used from Mediatech, Inc. (Manassas, Va.). GelBond® PAG Films and Gel Slick® glass plate coating were used from Lonza (Base, Switzerland). Photo-masks were designed using CleWin (PhoeniX Software, Enschede, Netherlands) and printed on Mylar transparencies at CAD/Art Services (Brandon, Oreg.)

Green fluorescent 15 µm FluoSpheres® were used for EOF visualization (Invitrogen Life Technologies Corporation, Carlsbad, Calif.). FluoSpheres® were sulfate-based microspheres and had a net negative charge at neutral pH. AlexaFluor 488 (AF488) conjugated Trypsin Inhibitor (TI*, 21 kDa), Ovalbumin (OVA*, 45 kDa), and Bovine Serum Albumin (BSA*, 67 kDa) were used from Life Technologies Corporation. Unlabeled BSA from Sigma and unlabeled OVA from Thermo Scientific (Rockford, Ill.) were used. Tris-glycine (10×, pH 8.3) native electrophoresis buffer was used from Bio-Rad Laboratories (Hercules, Calif.) and 1 M Tris-HCl (pH 8.6) was used from bioWORLD (Dublin, Ohio). The protein ladder used in this study included 500 nM each of TI*, OVA*, and BSA* fluorescently labeled with AF488 in the Tris-glycine buffer. Fluorescently labeled proteins were denoted with a "*". Unless otherwise noted, all sample buffers contained 1× Tris-glycine (25 mM Tris, 192 mM glycine, pH 8.3), 10% glycerol and 0.5% Triton X-100 and all gel buffers contained 1× Tris-glycine and 20% glycerol. Separations were in native conditions, which was suitable for measuring protein complexes. Separations may be performed using SDS PAGE with the fsPAGs.

The PAG precursor solution used in fabrication was prepared fresh for each device and contained acrylamide (10% T to 20% T), cross-linker (bis-acrylamide at 3.33% C), and a photo-initiator (1% w/v VA-086). Immediately prior to photo-polymerization, the precursor solution was pipetted into an Eppendorf tube and degassed for 1 min under vacuum with sonication.

fsPAGE Operation

Figure 5:
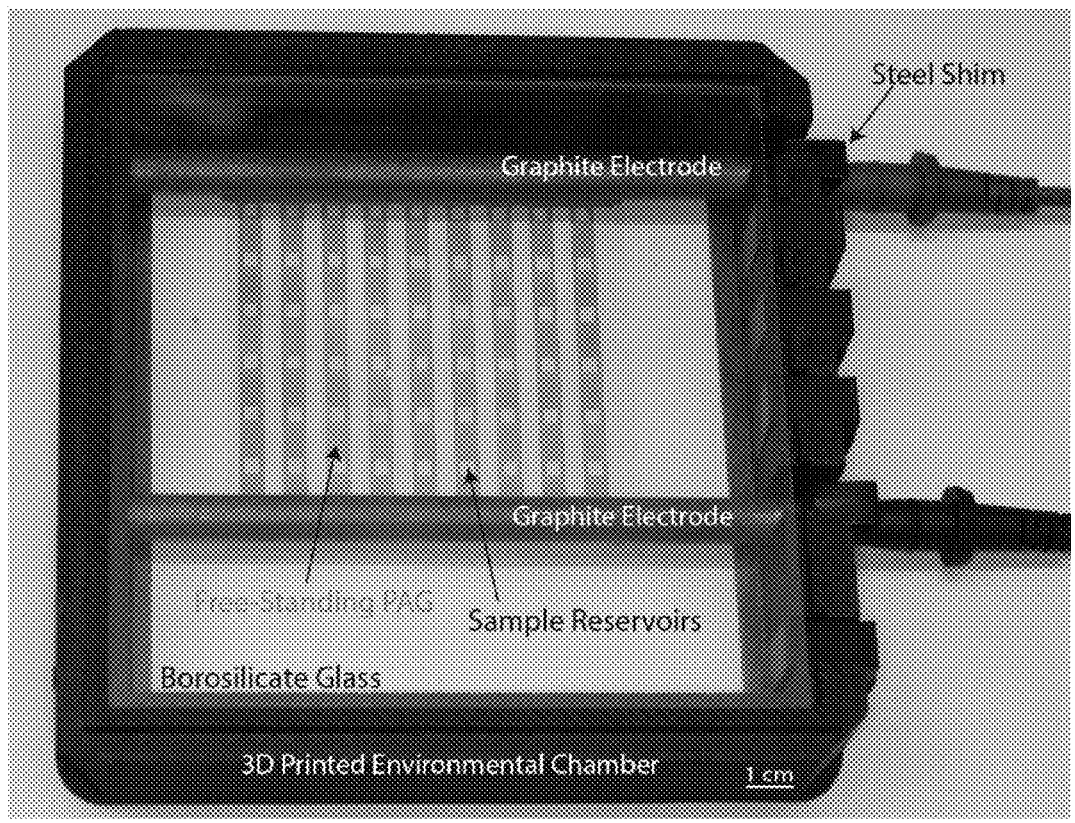
FIG. 5 shows an image of an environmental chamber, which was used to minimize evaporation during free-standing polyacrylamide gel electrophoresis (fsPAGE), according to embodiments of the present disclosure.

Operation of fsPAGE was performed in the environmental chamber shown in FIG. 5. A 3D printed holder was designed in Solidworks (Waltham, Mass.) and 3D printed using a uPrint® from Stratasys (Eden Praire, Minn.). Graphite bar electrodes (#1702980) and M4 to banana plug connectors (#9007004) (Bio-Rad Laboratories) were used. Steel shim stock with a 0.1 mm thickness (OnlineMetals.com, Seattle, Wash.) was used. Borosilicate glass plates with 1 mm thickness (CBS Scientific, San Diego, Calif.) were used. Electrode wicks (300 mm×6 mm×1 mm) (Serva, Heidelber, Germany) were placed between the fsPAG and the graphite electrodes.

The fsPAG devices were soaked in run buffer for 5 min. When removed, the back side of the GelBond® was dried with a tissue (Kimwipe®, Kimberly-Clark Corporation, Neenah, Wis.) and placed on top of a piece of borosilicate glass (CBS Scientific, San Diego, Calif.). Residual buffer was wicked from the reservoirs and from the top of the PAG surfaces using a tissue. Electrode wicks (Serva, Heidelber, Germany) were wetted in run buffer, excess buffer was removed with a tissue, and the damp electrode wicks were then placed on top of the gel contact pad. Protein samples were pipetted into the reservoirs and the device was placed in the environmental chamber. Graphite electrodes (Bio-Rad Laboratories) were placed in contact with the electrode wicks. The environmental chamber was sealed with a borosilicate glass plate and a voltage was applied with a PowerPac® HV power supply (Bio-Rad Laboratories) to initiate electrophoresis.

Imaging

Imaging (e.g., as shown in FIGS. 7A-7E, 8A-8B and 9A-9C) was conducted on an inverted epi-fluorescence microscope (Olympus IX-70) equipped with a Peltier cooled charge-coupled device (CCD) camera (CoolSNAP HQ2, Roper Scientific, Trenton, N.J.) and a 2× objective (PlanApo, N.A.=0.08, Olympus, Center Valley, Pa.). Camera exposure times were 300 ms, unless otherwise indicated. Illumination was from an X-Cite® exacte mercury lamp (Lumen Dynamics, Mississauga, Canada) filtered through a XF100-3 filter (Omega Optical, Battleboro, Vt.). Large area imaging (e.g., as shown in FIGS. 10A-10C and 11A-11D) was performed using a ChemiDoc XRS+ trans-illuminator with an XciteBlue conversion screen and standard ChemiDox XRS+ 548-630 nm emission filter (Bio-Rad Laboratories).

Image analysis was performed with ImageJ software (NIH, Bethesda, Md.). Intensity plots were extracted across the transverse axis of the separation gel, thereby including any added dispersion from protein band bowing. Post processing was performed using an in-house algorithm implemented with MATLAB® (MathWorks, Natick, Mass.).

To create particle streak lines in the electroosmotic flow (EOF) studies, exposure times of 6 s were used with an image acquisition rate of one frame per 7 s. During image collection, the applied electric potential was removed midway through exposure and the beads slowed to a stop during the acquisition, yielding an apparent "head" and "tail" for each migrating bead. The circular head represented the final location of a bead while the tail indicated the beads path and relative velocity during motion, approximating transport in a manner analogous to a velocity vector field.

Results and Discussion

Fabrication of fsPAG Microstructures

Figure 6:
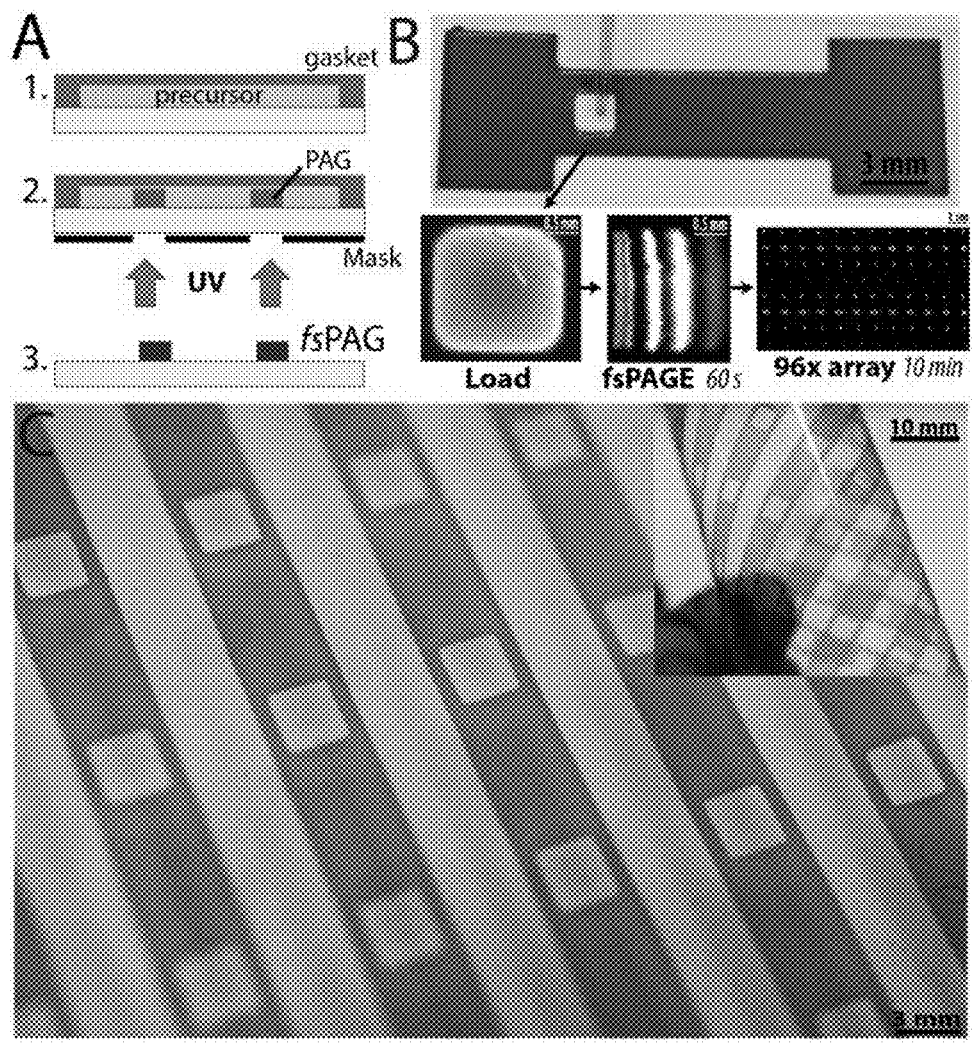
FIG. 6A shows a process flow schematic for free-standing polyacrylamide gel (fsPAG) fabrication, according to embodiments of the present disclosure. Fabrication was completed in 10 min and included three steps: 1. Polyacrylamide precursor solution was sandwiched between a gasket and a GelBond® substrate; 2. The solution was exposed to UV light through a photo-mask; and 3. Excess precursor solution was washed away.
FIG. 6B shows images of fsPAGE, where a protein sample was pipetted directly into a reservoir and then electrophoretically transported into and separated by the fsPAG structure with an applied voltage to the fsPAGs contact pads.
FIG. 6C shows an image of 120 μm tall fsPAG microstructures patterned over a support for use in multiplexed protein electrophoresis on fsPAG arrays operated with a single anode-cathode pair, according to embodiments of the present disclosure.

For protein PAGE analysis, fsPAG microstructures that included a sample injection well and separation lane were fabricated. The fsPAG fabrication process is shown in FIG. 6A (see also FIG. 14). After mask design and printing, the first fabrication step was sandwiching a PAG precursor solution (containing photo-initiator) between a support surface and a lid (e.g., a polydimethylsiloxane, PDMS, gasket); here, the lid was coated with Gel Slick® to minimize gel attachment. The support surface presented exposed unsaturated hydrocarbons (e.g., surface alkene groups) for covalent bonding with the PAG during the free-radical polymerization process. A GelBond® PAG support was used. The desired chemistry can also be coated on glass and polymer surfaces. The precursor solution was exposed to UV light through a mask to photo-polymerize the desired fsPAG structure geometries. Exposure proceeded for 35 s using a 13 mW/cm$^2$ UV intensity and for up to 240 s using a lower UV intensity of 8 mW/cm$^2$ (measured by a UV light meter). The lid was removed and unpolymerized precursor solution was washed away leaving behind the three-dimensional fsPAG microstructures. The UV intensity and time were optimized for a given gel density, and the fabrication method had yields of >95%, for n ~100. For zone electrophoresis devices, structures with scale heights (120 µm) and mm-scale in-plane features were fabricated. Using this fabrication protocol, fsPAG structure with a minimum features size of 75 µm in width were produced. The PAG microstructure height (z-axis) was adjusted by modifying gasket height with spacers. The z-axis resolution was determined by the precision of spacer height.

Figure 14:
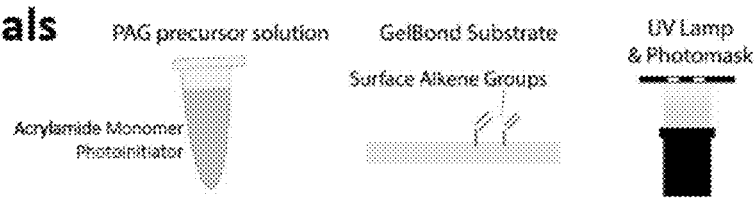
FIG. 14 shows a schematic of a workflow for the fabrication of free-standing polyacrylamide microchannel arrays, according to embodiments of the present disclosure.
Figure 14:
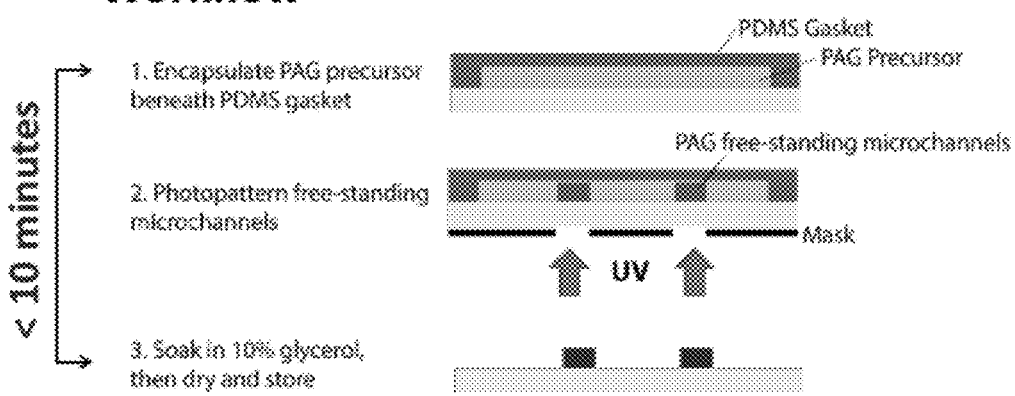

FIG. 14 shows another schematic of a workflow for the fabrication of free-standing polyacrylamide microchannel arrays as described above.

If a buffer exchange step was desired prior to PAGE, a 5 min soak in the run buffer was performed. All devices used in this study were stored in run buffer solution prior to use. From start to finish, the fsPAG fabrication process took less than 10 min. Fabrication of fsPAG microstructures did not require mold fabrication, as the features were directly photopatterned on the support substrate.

Log Linear Protein Sizing

Figure 18:
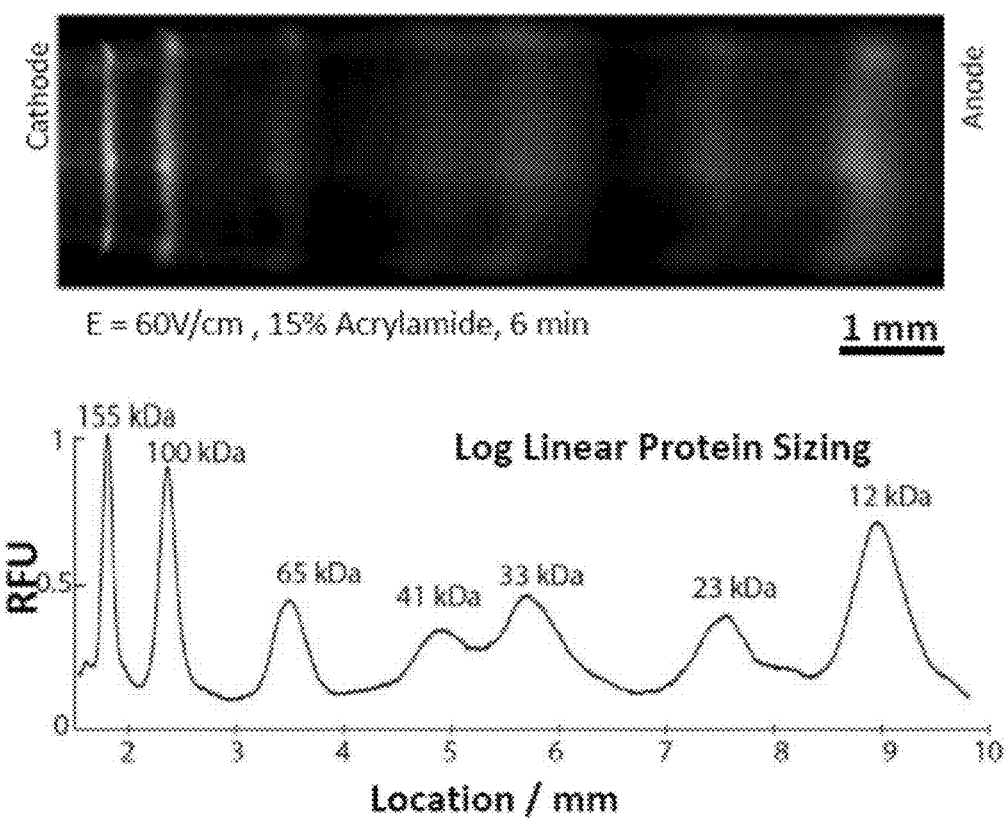
FIG. 18 shows an image (top) and graph (bottom) of the separation of a 7 protein ladder in a free-standing polyacrylamide microchannel array, according to embodiments of the present disclosure. The 7 protein ladder was resolved in 1 cm and in 6 minutes using 15% acrylamide and E=60V/cm.

FIG. 18 shows an image (top) and graph (bottom) of the separation of a 7 protein ladder in a free-standing polyacrylamide microchannel array. The 7 protein ladder was resolved in 1 cm and in 6 minutes using 15% acrylamide and E=60V/cm. Log linear protein sizing was observed.

Sample Injection in fsPAGE

Injector Geometry

Using the fsPAG fabrication process, fsPAG microstructures were fabricated with a sample injector geometry analogous to slab-gel PAGE formats: a free solution sample reservoir (i.e., an area with no polymerized gel) fabricated in-line with the PAG separation axis (FIG. 6B). In-line injection in fsPAG microstructures allowed one-step injection to fsPAGE, sample stacking at the reservoir-separation gel interface, and simplified the microstructure geometry and footprint, which facilitated multiplexing. To load the fsPAG microstructure, an aliquot of sample (1 µL) was pipetted directly into the free-solution reservoir. To inject sample, voltage was applied at the terminal ends of the fsPAG structure, causing the loaded sample volume to be injected into the fsPAG for the assay. Reservoir array layouts with a standard pitch (well-to-well spacing) facilitated integration of the fsPAGE platform with common fluidic handling systems (FIG. 6C). The fsPAGE loading volume could be changed by adjusting reservoir dimensions. In some instances, sensitivity of the assay depended on sample consumption.

Sources of Injection Dispersion

Given the geometry and materials characteristics of the sample reservoir, a surface charge may be present on the bottom of the sample reservoir from the GelBond® film. This charged material could, in turn, support EOF during application of an electric field. Given the closed geometry of the sample reservoir, recirculation arising from EOF during injection—if not corrected during sample stacking—could induce dispersion in the subsequent fsPAGE assay as the sample front migrated into the fsPAG.

Figure 7:
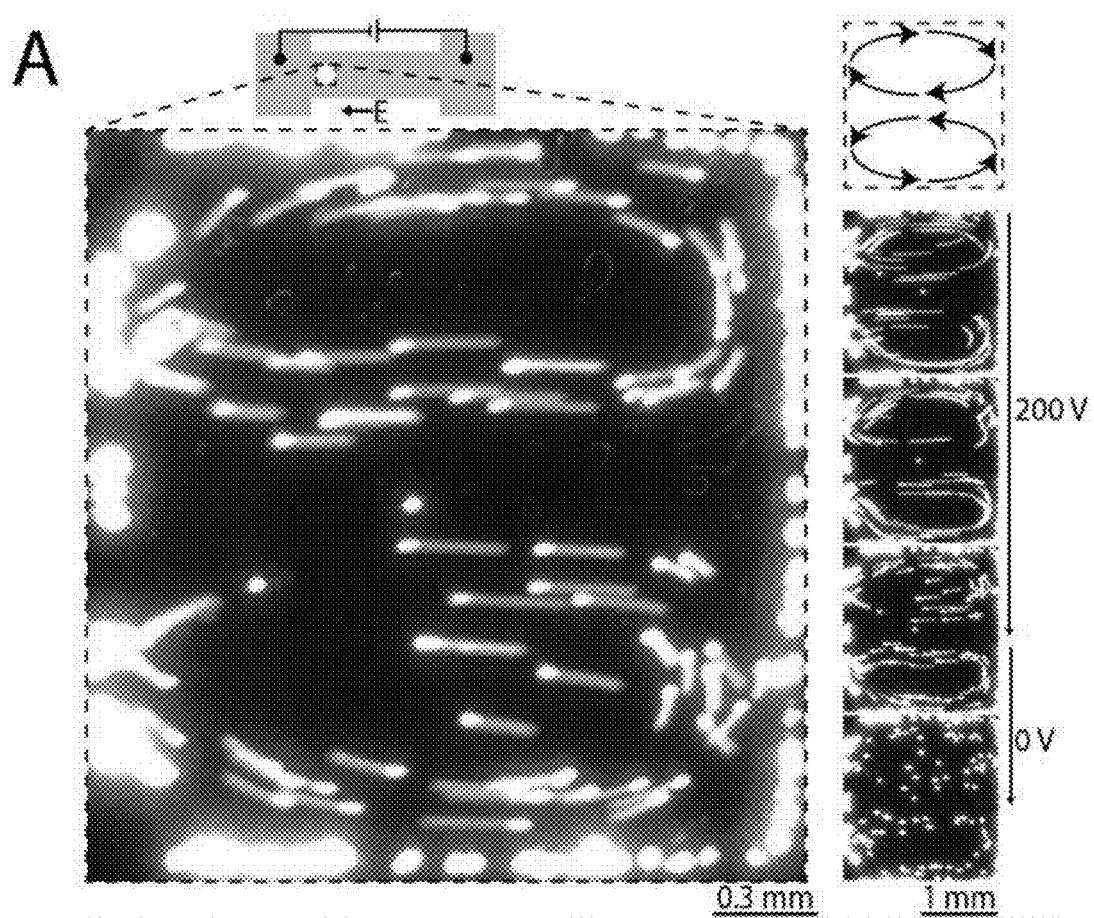
As shown in FIG. 7, the improvement was from a reduction of both EOF and protein adsorption in the reservoir.

To investigate the presence of EOF during electrokinetic sample injection from the reservoir into the fsPAG, experiments were performed to track particles in the reservoir (FIG. 7A). A solution of 15 µm diameter fluorescent microbeads was pipetted into the 2 mm×2 mm reservoir and an injection potential was applied (V=200 V). Epi-fluorescence imaging of bead streak lines showed two axially symmetric vortices in the reservoir. At the reservoir centerline, both vortices flowed towards the cathode, and recirculated towards the anode at the edges of the reservoir. The polyester support was coated with a layer of adherent resin with ethylenically unsaturated groups. The GelBond® surface was hydrophilic, with a water contact angle of less than 10°, thus, surface polarization may be present.

Experiments were performed to determine the effect of reservoir EOF on sample injection into a 15% T PAG at 100 V/cm from the 2 mm×2 mm reservoir. Injection for both discontinuous and homogeneous electrophoresis was analyzed in FIG. 7B and FIG. 7C, respectively. In discontinuous electrophoresis, transient isotachophoresis was used to preconcentrate a sample within the reservoir region between a trailing ion (glycine) and a leading ion (Cl) prior to a PAGE separation. The increased local electric field in an isotachophoretic stack resulted in enhanced EOF. Images of the transient isotachophoresis injection of OVA* show a non-ideal injection, with a streak observed along the reservoir centreline, which was in agreement with the qualitative bead tracking in FIG. 7A. Both results indicated that the GelBond® had a surface charge that induced EOF. In the homogeneous electrophoretic injection, the desired axially orthogonal OVA* band was observed, but streaking was seen along the edges of reservoir. The reduced band distortion in the homogeneous system was due to the combination of a slower EOF and a shorter reservoir migration time. As was relevant to the isotachophoretic injection mode, suppression of EOF may reduce or eliminate the distorted and dispersive sample zone injected into fsPAGE.

Figure 12:
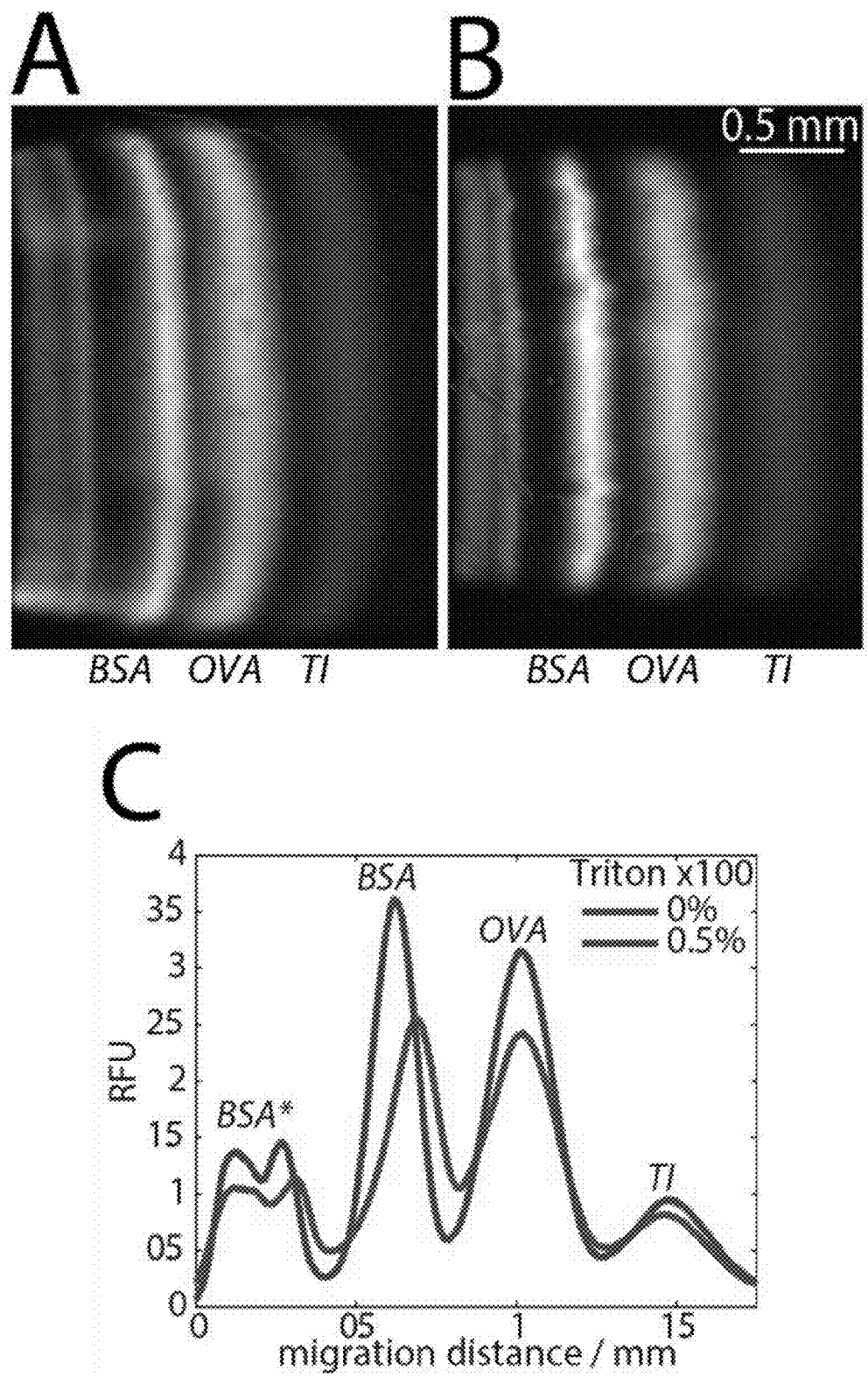
FIGS. 12A and 12B show images of the separation of a protein ladder in a 20% T fsPAG at 100 V/cm, which was performed without an EOF suppressor (FIG. 12A) and with 0.5% Triton X-100 (FIG. 12B).
FIG. 12C shows a graph of the intensity plot profiles of the corresponding images, which were aligned at the point where OVA* had migrated 1 mm, e.g., 40 seconds for the suppressor-less separation and 51 seconds for the 0.5% Triton x100 separation. The 0.5% Triton x100 increased the solution viscosity and reduced migration velocities by ~25%. In the separation with the EOF suppressor the protein peaks were both better resolved and larger than the separation without an EOF suppressor.

In the presence of surface charge in the reservoir, protein adsorption to the reservoir may result in either dispersive sample injection or sample mass loss. Adsorption was apparent for both the discontinuous and homogeneous injections with residual proteins seen in the reservoir 30 s after the electric field was applied. The protein adsorption was evaluated in FIG. 7C by monitoring fluorescence signal in the sample reservoir during electrophoresis. Upon application of the sample injection voltage, a 75% reduction of the initial fluorescence signal was observed in the first 20 s. Continued monitoring of the reservoir fluorescence showed an exponential decay in signal. The steady decrease in signal indicated gradual leaching of retained sample off of the surface over time. As sample adsorption to the reservoir material resulted in sample loss and non-ideal sample injection (e.g., sample streaking from the reservoir), capillary EOF suppressors were applied to the reservoir, as shown in FIGS. 7D and 7E for discontinuous and homogenous electrophoresis, respectively. For homogeneous electrophoresis with EOF suppression additives, 0.35% Brij or 0.5% Triton X-100, >95% of sample fluorescence signal exiting the reservoir was observed in the first 20 s of field application. The resulting injection of a discrete, well defined sample zone was observed when the suppressor was only in the run buffer, only in the sample buffer, or in both. In FIG. 12 a 20-30% improvement in separation performance and a 16-42% reduction of sample mass loss was observed with an EOF suppressor additive in homogeneous electrophoresis. For discontinuous electrophoresis, protein adsorption was also minimized with the addition of an EOF suppressor, but the OVA* protein band was still distorted by EOF. In combination with EOF suppressors, the band distortion can be minimized in discontinuous injection by reducing the electric field (FIG. 13), but a trade-off was made with the duration of the injection. In cases where EOF was not desired, coating the GelBond® substrate with a neutral polymer to minimize EOF in discontinuous electrophoresis may be used. In cases where EOF-induced stirring in the reservoir was desired (e.g., sample preparation, timed reactions), EOF can alternately be enhanced through selection of charged coatings and/or spatial patterning.

fsPAG Sample Stacking

Figure 8:
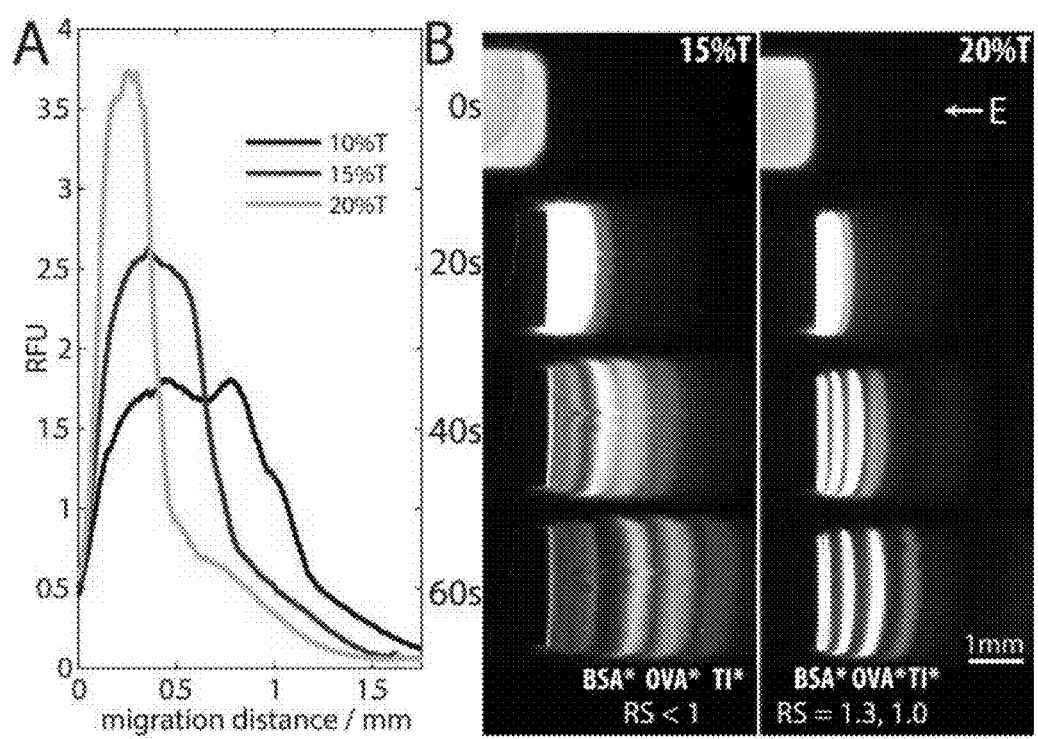
FIGS. 8A and 8B show and images of sample stacking in a 20% T fsPAG, which facilitated the separation of a protein ladder over 2 mm in 60 s.

The free-solution sample reservoirs acted in an analogous manner to a stacking gel. The sample migrated at its free-solution mobility ($\mu_o$) in the reservoir but slowed down after it entered the PAG molecular sieve to an in-gel mobility ($\mu$). The degree of sample stacking was equivalent to the ratio of these mobilities ($\mu_o/\mu$), effectively enriching the sample and reducing the peak width by the same ratio. In PAGE, in-gel mobility was determined using the Ferguson relationship, $\mu=\mu_o 10^{-KT}$, where K is the retardation coefficient of an analyte and T is the total acrylamide concentration in the precursor solution (gel density). An increase in gel density may improve stacking and separation performance until proteins are excluded from the molecular sieving matrix. To test the relationship between fsPAG pore-size and stacking, a sample of 500 nM OVA* was electrophoretically loaded at 100 V/cm from a 2 mm×2 mm reservoir into fsPAG structures of 10% T, 15% T and 20% T PAG. FIG. 8A shows intensity plots of the first 1.5 mm of migration in each gel after 14 s. RFUs were normalized to the initial intensity within the reservoir to correct for any variation in loaded sample volume. As expected from the Ferguson relationship, stacking was most significant in the 20% T experiments with sample enrichment of 3.83±0.69 and a half-peak width of 308.7±19.4 µm. The 15% T and 10% T PAGs showed enrichments of 2.63±0.14 and 1.89±0.24 with a half-peak width of 627.0±40.4 µm and 1021.9±106.7 respectively.

Experiments were performed to study stacking in fsPAGE separations. The protein ladder was electrophoresed into each gel density at 100 V/cm and the separation resolution, RS, was monitored. RS=X/4σ, where X is the distance between the neighboring peak maxima and 4σ is the average peak width of neighboring peaks. In the 10% T PAG, no protein species were resolved (resolution was defined as RS≥1) over the total 9.5 mm length. In FIG. 8B, montages for the first 60 s of the 15% T and 20% T separations are shown. In the 20% T case, both the BSA*-OVA* and OVA*-TI* separations were completed in 60 s with RS values of 1.3 and 1.0 and in separation lengths of 1 mm and 1.7 mm, respectively. In contrast, the separations were still unresolved in the 15% T PAG at 60 s. The BSA*-OVA* species eventually resolved in 100 s at a separation length of 3.4 mm, and the OVA*-TI* was nearly resolved (RS=0.92) at 380 s in 9.1 mm. This geometry and performance would correspond to 25 unique separations within the length of a typical 10 cm slab-gel lane, assuming a 2 mm reservoir length and a separation length of <2 mm (e.g., 20% T case). These results indicated that sample stacking facilitated high resolution protein separations and multiplexing. A maximum electric field of 100 V/cm was used in this study for fast electrophoretic separations with minimal gel shrinkage over the course of a 20 minute separation. By increasing the electric field to 250 V/cm TI*, OVA*, and BSA* were resolved in less than 15 seconds, but an increase in dispersion was observed for separations longer than 15 s, which may be due to gel drying (observed physically and through electric current).

Figure 9:
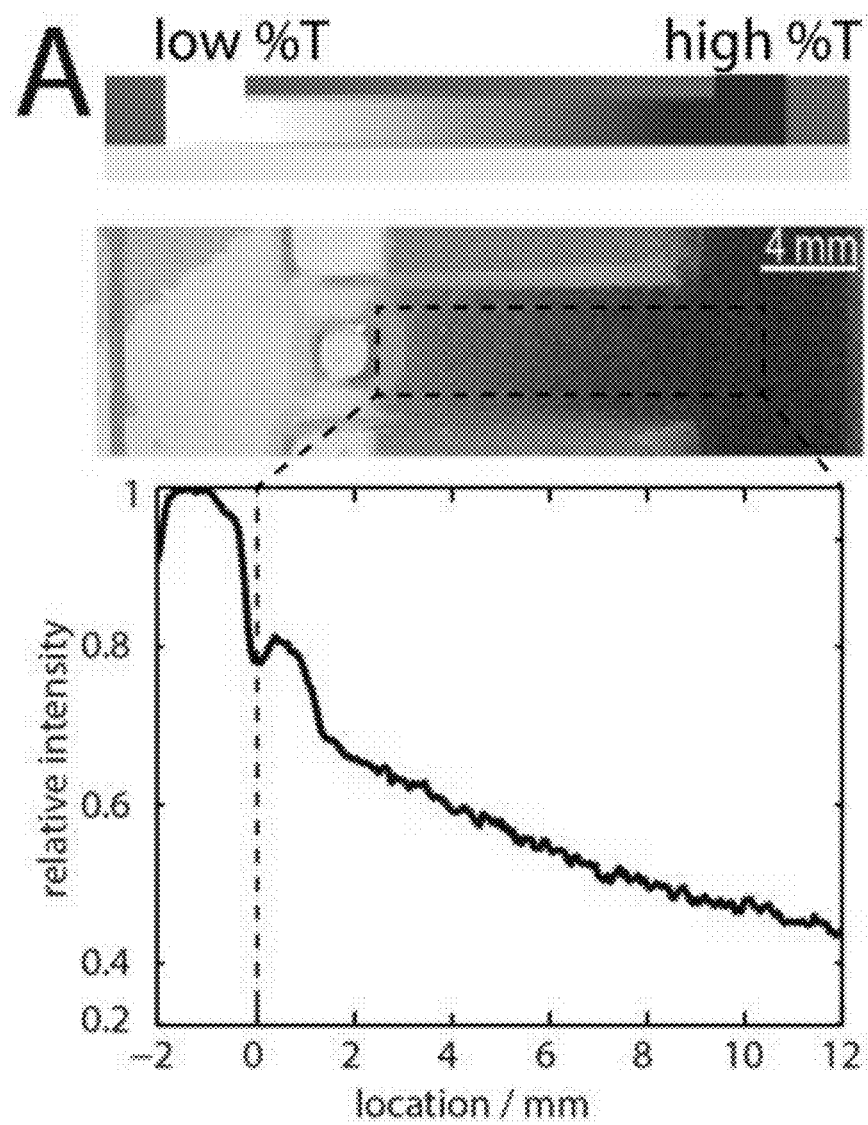
FIGS. 9A and 9B show images and a graph, where gradient fsPAG suppressed protein dispersion over an 8 min separation.
FIG. 9C shows a graph of RS plotted over the course of the experiment for the BSA*-OVA* and OVA*-TI* separations for both gel conditions. In the gradient gel, RS increased with time due to the growing peak to peak separation between species and minimal bandwidth growth. All protein species were baseline resolved (RS=1.5) in 80 s. The uniform gel had a substantially constant RS after about 100 s due to bandwidth growth. The BSA*-OVA* species were baseline resolved in 110 s, while the OVA*-TI* were not baseline resolved.

While the TI*, OVA*, and BSA* separation was completed in 1 minute, if the assay was continued for 5 minutes (as shown in FIG. 9) the commonly observed BSA dimer and trimer (BSA$^2$ and BSA$^3$, 138 and 207 kDa, respectively) were resolved. The 5 minute separation over a 21-207 kDa size range in 1 cm was comparable to the dynamic range seen in many 10 cm uniform slab-gel separations.

Figure 15:
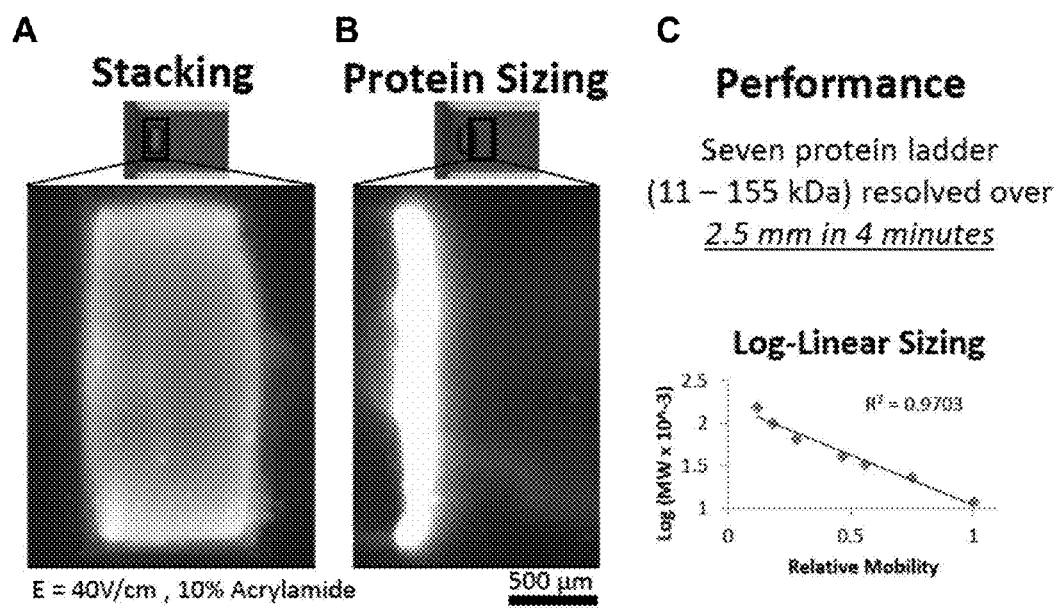
FIG. 15A shows an image of protein stacking in a free-standing polyacrylamide microchannel array, according to embodiments of the present disclosure.
FIG. 15B shows an image of protein sizing in a free-standing polyacrylamide microchannel array, according to embodiments of the present disclosure.
FIG. 15C shows a graph of the performance (Log (MW×10$^{-3}$) vs. Relative Mobility) for a free-standing polyacrylamide microchannel array, according to embodiments of the present disclosure.

FIG. 15A shows an image of protein stacking in a free-standing polyacrylamide microchannel array (10% T acrylamide) using an E=40 V/cm. FIG. 15B shows an image of protein sizing in the free-standing polyacrylamide microchannel array. FIG. 15C shows a graph of the performance (Log(MW×10$^{-3}$) vs. Relative Mobility) for the free-standing polyacrylamide microchannel array. A 7 protein ladder (11 kDa to 155 kDa) was resolved over 2.5 mm in 4 minutes ($R^2$=0.9703).

Gradient fsPAGE

While uniform pore-size PAGs allowed electrophoretic separation of analytes with sufficiently large mobility differences, resolving analytes over a broad range of mobility differences was performed using gradient PAG separations. In a decreasing pore-size gradient PAG, migrating analytes experience an increasing PAG density which acts to stack the zone as species migrate down the separation axis. This continual stacking reduces peak width and, thus, increases RS.

FIG. 9A shows the fabrication of a decreasing 10% T to 20% T gradient pore-size fsPAG using a gasket with two inlets. Precursor solution for a low % T PAG was placed in one inlet (left) and precursor for a high % T PAG was placed in the other inlet (right). A 15 min diffusion step allowed formation of gradient in % T along the separation axis. After diffusion established the gradient, UV cross-linked the precursor solution (8 mW/cm$^2$ for 4 min) resulting in an fsPAG with non-uniform PA pore-size. For visualization, disodium 6-hydroxy-5-[(2-methoxy-4-sulphonato-m-tolyl)azo]naphthalene-2-sulphonate (Allura Red AC dye) was added to the high % T precursor to visualize an approximation of the diffusive gradient formation process. Allura Red AC has a molecular weight of 496 Da, seven-times larger than acrylamide monomer, thus allowing an estimate of the gradient formation process. The resulting fsPAG structure and the Allura Red AC concentration distribution is shown in FIG. 9A. The gel was then soaked in buffer for 10 hours to remove residual Allura Red AC.

After fabrication of a gradient fsPAG, separation performance of the gradient fsPAGE was compared to a uniform fsPAGE. A protein ladder was analyzed using a uniform 20% T fsPAG and a 10% T-to-20% T decreasing pore-size fsPAG (E=100 V/cm), as shown in FIG. 9B. In the uniform gel, peak widths increased over the separation time. In contrast, in the decreasing pore-size fsPAG, a slight reduction in peak widths was observed over time, due to the stacking nature of the decreasing pore-size fsPAG. Between 100 s and 500 s, protein velocities reduced from 17.2 µm/s to 4.3 µm/s, 13.3 µm/s to 3.4 µm/s, and 7.7 µm/s to 2.0 µm/s for TI*, OVA*, and BSA*, respectively. As a result, the gradient fsPAGE RS was enhanced compared to the uniform fsPAGE results. At 500 s of separation time, the uniform fsPAGE assay resolved the smaller molecular mass OVA*-TI* peak pair (RS=1.0), whereas in the gradient gel, the same pair showed more than complete baseline resolution (RS=4.4), see FIG. 9C. Baseline resolution for the smaller molecular mass OVA*-TI* pair was reached (RS=1.5) after just 80 s of separation time in the gradient fsPAGE assay.

Multiplexed fsPAGE

Figure 10:
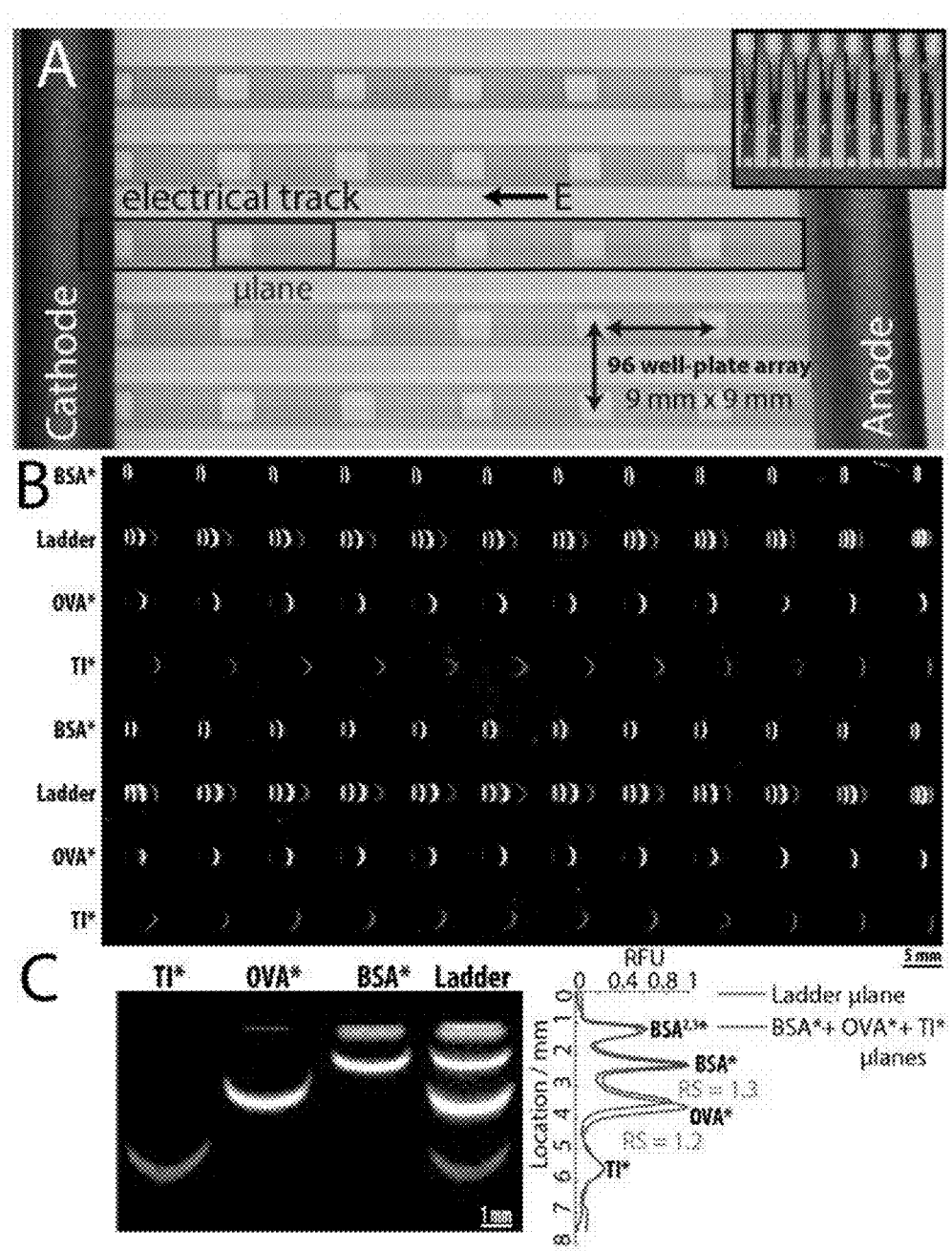
FIG. 10A shows a fsPAG array used for separating 96 discrete samples separated in less than 10 min, according to embodiments of the present disclosure. fsPAG arrays were fabricated to correspond to a 96-well plate layout. Reservoirs were in an 8×12 array with 9 mm spacing, which facilitated sample delivery using a 12-channel pipette. The fsPAG microchannels were addressed with electrical tracks that spanned the two electrodes and operated with a standard slab-gel power supply.
FIG. 10B shows an image of a 96-plex 20% T fsPAGE separation concluded in 9.6 min. The array was loaded with 4 different AF488 labelled samples: TI* (rows 4 and 8), OVA* (rows 3 and 7), and BSA* (rows 1 and 5), and a protein ladder (rows 2 and 6).
FIG. 10C shows an image (left) and graph of fluorescence (RFU) vs. location (mm) (right) showing separation uniformity compared along one column in the array. An intensity profile of a ladder microchannel was overlaid with the summation of intensity profiles for the TI, OVA, and BSA* microchannels, which showed less than 5% variation in protein migration.

The fsPAGE assay was scaled-up for multiplexing through concurrent assay operation. The full array was operated with a single slab-gel power supply and two electrodes. As shown in FIG. 10A, electrical tracks connected the anode to cathode, with each electrical track including more than one fsPAGE. A single fsPAGE module consisted of a rectangular sample reservoir and contiguous free-standing separation gel; the module is termed a "µlane" or "microlane" or "microchannel" for convenience. Several µlanes in series were included each electrical track. Electrical tracks connected to the same cathode and anode hardware, allowing concurrent separations in each µlane, as well as in each electrical track. The sample was diluted in a loading electrophoresis buffer prior to sample-loading. Therefore, reservoir conductivity was determined by the electrophoresis buffer as opposed to the protein sample, which minimized potential electric field variations along an electrical track. Inclusion of internal migration standards facilitated sample to sample protein migration comparisons. Sample reservoir spacing corresponded to the registration of a standard 96 well-plate, thus facilitating the use of fsPAGs with standard laboratory liquid handling technologies (e.g., handheld multichannel pipettors, automated robotic fluid delivery systems, etc.).

A 96-plex PAGE separation of various samples was performed in 9.6 min using the fsPAGE array. Samples in the 96 unique reservoirs were electrophoresed into 20% fsPAGs at 63 V/cm. Assays were performed on each individual ladder protein (TI*, OVA*, BSA*) and the ladder mixture. In FIG. 10C, the repeatability between µlanes within a row was determined by comparing the separations in column 8, rows 3-6. The ladder separation was compared to the sum of the µlanes including TI*, OVA*, and BSA* alone. The overlay showed a close migration match between the µlanes with a migration percent variation of 1.2%, 4.2% and 3.8% for the TI*, OVA*, and BSA* species, respectively. In addition, the BSA*-OVA* and OVA-TI* separations were resolved with RS values of 1.3 and 1.2, respectively.

Protein mobility in µlanes positioned in the middle of the fsPAG array was higher than mobilities observed in µlanes along the boundary. For example, the BSA* on the top row migrated 25% slower than in row 5 and TI* in the bottom row migrated 15% slower than in row 4. The boundary dependent mobility likely arose from increased evaporation along the edges of the array resulting in a denser PAG. Our non-uniform sieve hypothesis was supported by the larger protein BSA* (67 kDa) experiencing a more significant mobility reduction than the smaller TI* (21 kDa), as the exponential Ferguson relationship would predict. Due to slower migration at the boundaries, variation across the 96-plex array was 17.1%, 11.5% and 15.1% for TI*, OVA*, and BSA*, respectively. Just considering the middle of the array—µlanes in rows 3-6 and columns 3-10—absolute mobility variation was reduced to 8.4%, 4.6% and 6.0% for TI*, OVA*, and BSA*, respectively. An internal standard may be included to account for µlane to µlane variation across the array. By considering the relative mobility to an internal standard such as OVA*, the percent variation across all ladder separations reduced to 6.2% for TI* and 3.2% for BSA*.

The experiments described above used a 96-plex fsPAG microtiter layout for a particular protein separation. Other array formats are possible, for example, in cases where an assay requires separating proteins over a large molecular weight range or a higher level of multiplexing (e.g., 384-plex). A modified design with longer separation channels or more reservoirs may be developed to address each specific need.

Figure 16:
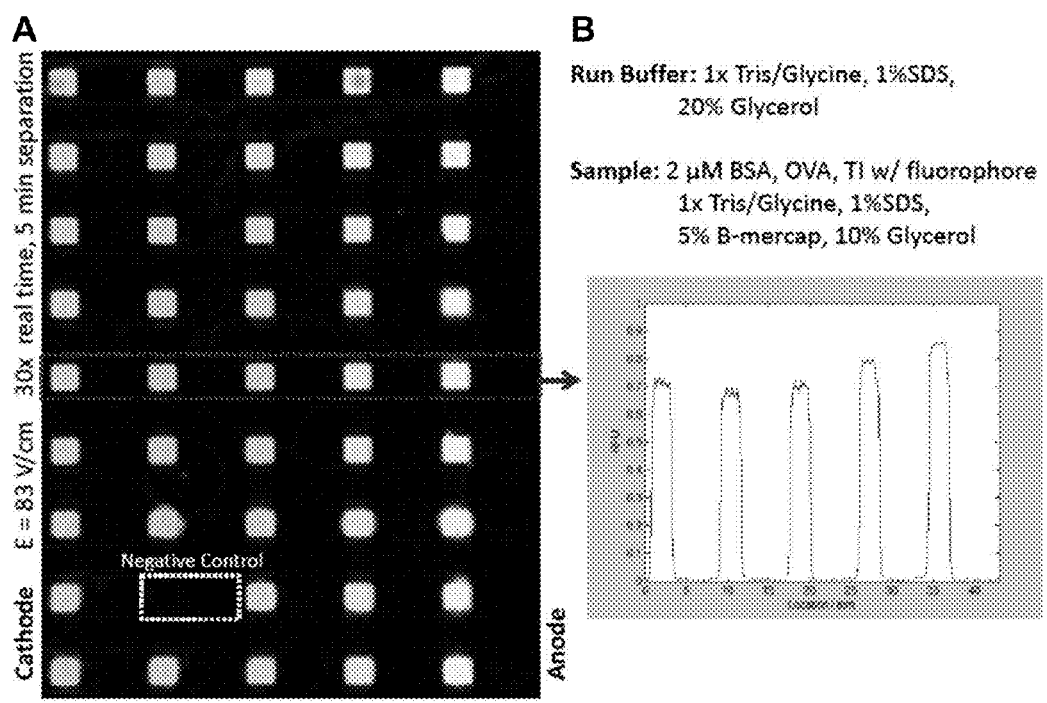
FIG. 16A shows an image of a free-standing polyacrylamide microchannel array, according to embodiments of the present disclosure.
FIG. 16B shows a graph of fluorescence vs. location for a row of the free-standing polyacrylamide microchannel array.

FIG. 16A shows an image of a free-standing polyacrylamide microchannel array configured for multiplex analysis. A 5 min separation of 2 µM BSA, OVA and TI with fluorophore in a sample buffer of 1% Tris/Glycine, 1% SDS, 5% β-mercap, and 10% glycerol was performed using E=83 V/cm with a run buffer of 1× Tris/Glycine, 1% SDS and 20% glycerol. FIG. 16B shows a graph of fluorescence (RFU) vs. location (mm) for a row of the free-standing polyacrylamide microchannel array.

Figure 20:
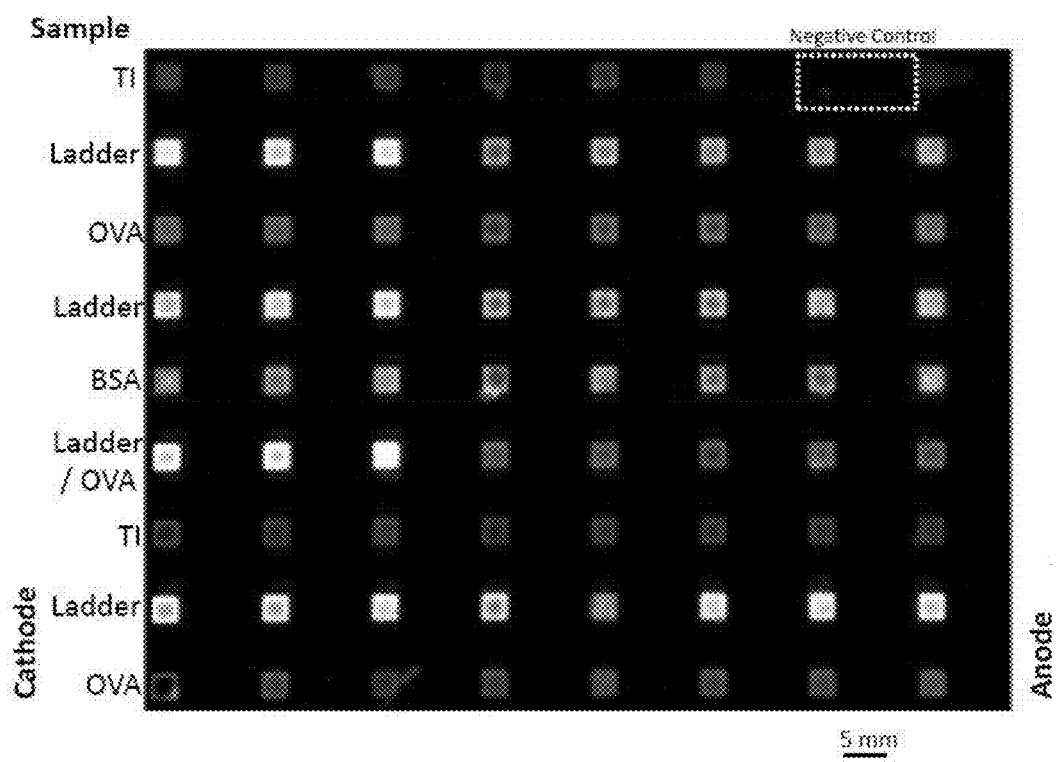
FIG. 20 shows an image of a 72-plex SDS PAGE (15% T polyacrylamide gel) free-standing microchannel array, according to embodiments of the present disclosure.

FIG. 20 shows an image of a 72-plex SDS PAGE (15% T polyacrylamide gel) free-standing microchannel array. The run buffer was 1× Tris/Glycine, 0.1% SDS and 20% glycerol. The sample buffer was 1× Tris/Glycine, 1% SDS, 5% β-mercap, and 10% glycerol. Samples analyzed were: (1) BSA (67 kDa); (2) OVA (45 kDa); (3) TI (21 kDa); and (4) protein ladder. The samples were analyzed using a SDS PAGE (15% T polyacrylamide gel) free-standing microchannel array with E=83 V/cm for 5 min.

Figure 21A:
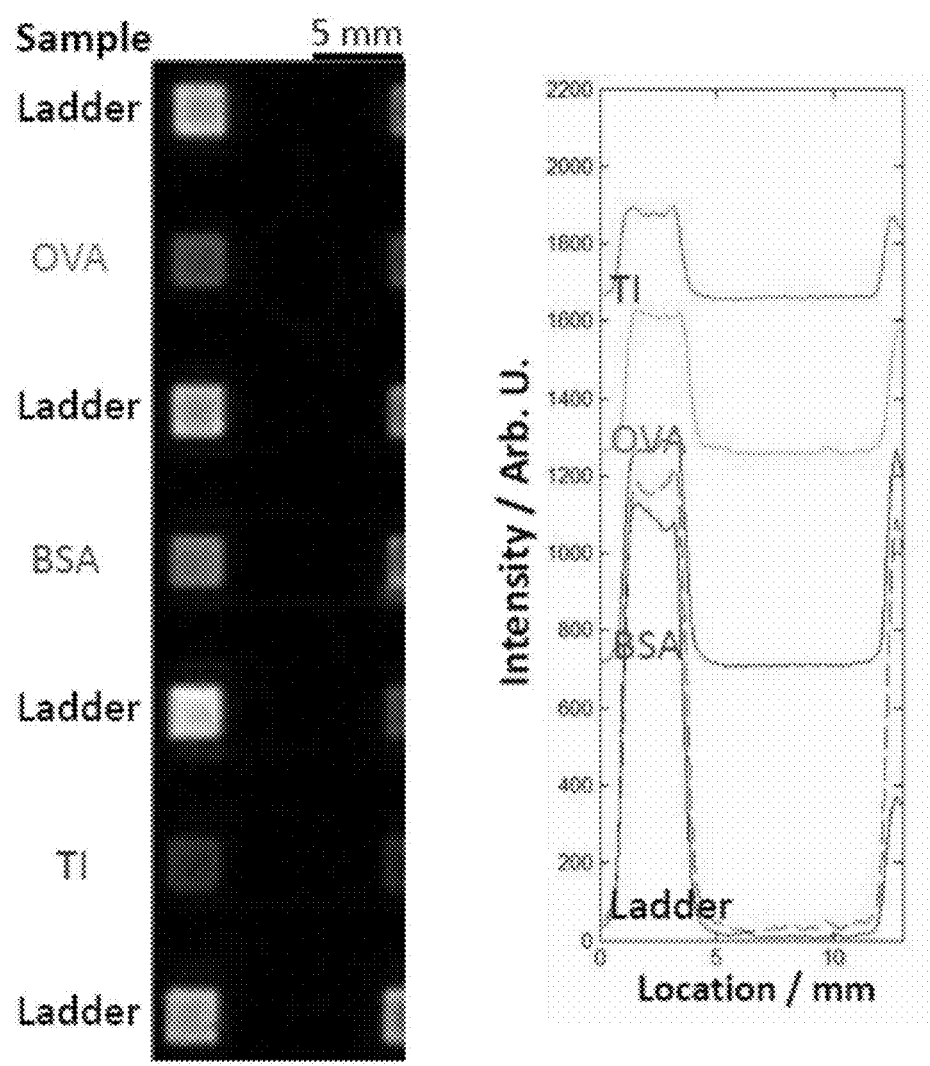
FIG. 21A shows an image (left) and corresponding graph of intensity (Absorbance units vs. location (mm)) (right) of multiplexed SDS PAGE using a free-standing microchannel array, according to embodiments of the present disclosure.
Figure 21B:
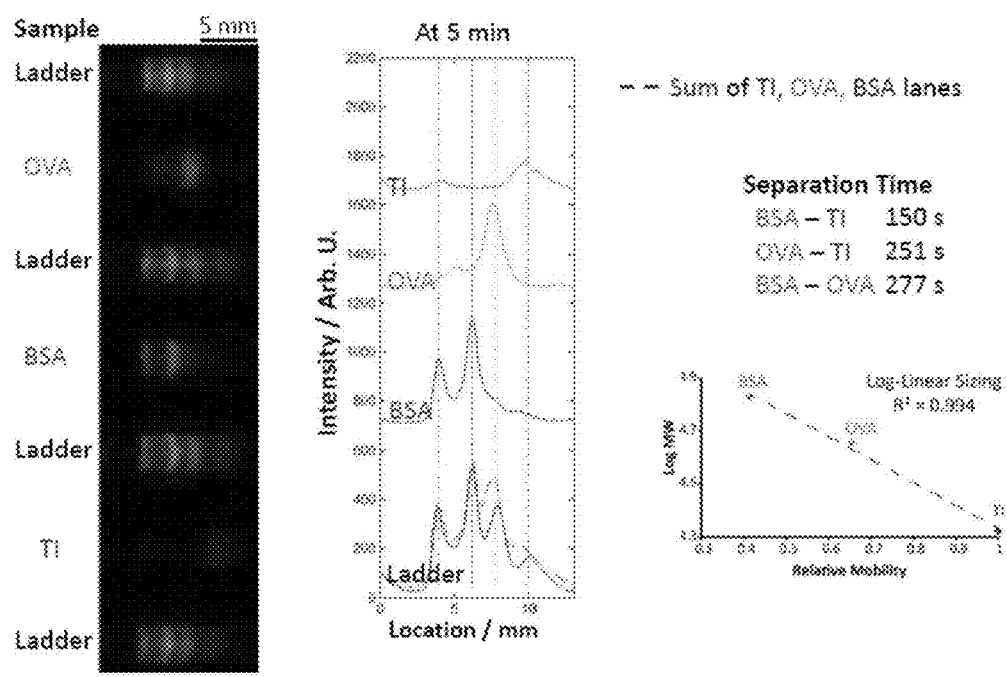
FIG. 21B shows an image (left) and corresponding graph of intensity (Absorbance units vs. location (mm)) (middle) of multiplexed SDS PAGE after 5 minute separation using a free-standing microchannel array, according to embodiments of the present disclosure.

FIG. 21A shows an image (left) and corresponding graph of intensity (Absorbance units vs. location (mm)) (right) of multiplexed SDS PAGE using a free-standing microchannel array. FIG. 21B shows an image (left) and corresponding graph of intensity (Absorbance units vs. location (mm)) (middle) of multiplexed SDS PAGE after 5 minute separation using a free-standing microchannel array. FIG. 21B (right) shows a graph of Log MW vs. Relative Mobility for BSA, OVA and TI.

Downstream Analysis

Figure 11:
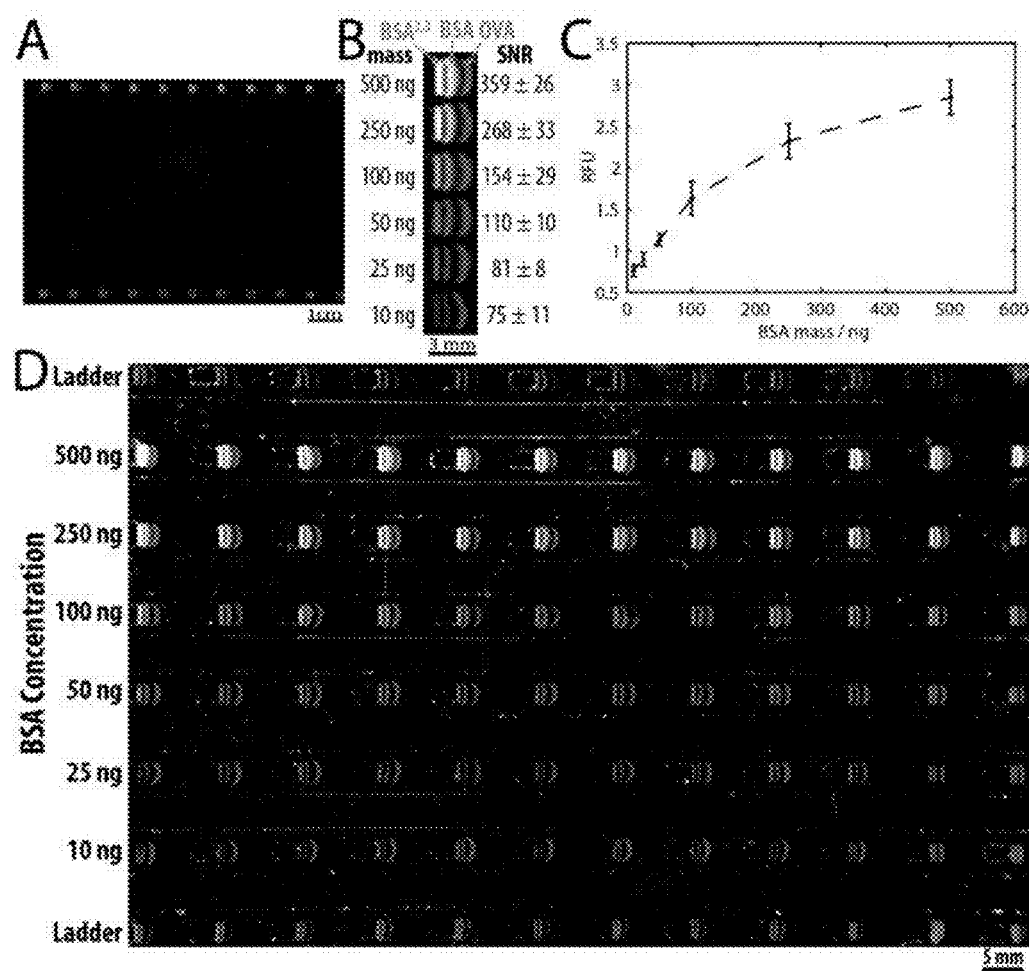
FIG. 11A shows an image of a fsPAG array used for separation and detection of 72 unlabeled native protein samples in a 7.5 hour assay, according to embodiments of the present disclosure. The 20 min, 39 V/cm separation was monitored by pre-labeled ladder proteins loaded into rows 1 and 8, and unlabeled BSA and OVA in rows 2 through 7.
FIG. 11B shows an image of the unlabeled protein samples fluorescently detected after a 6 hour stain with SYPRO Ruby.
FIG. 11C shows a graph of fluorescence (RFU) vs. BSA mass (ng) for various BSA concentrations, ranging from 500 ng to 10 ng, which were normalized to the OVA internal standard.
FIG. 11D shows an image of the fsPAG array, which was used for multiplexed quantification of unlabeled protein samples.

The fsPAG platform facilitates microfluidic multiplexing in a format amenable to post processing reagents and tools, such as a protein stain. In FIG. 11A, a 20 min separation was performed at 39 V/cm in a 20% T 96-plex fsPAG array and monitored with a pre-labeled ladder loaded into rows 1 and 8. Afterwards, the fsPAGE device was fixed in a solution of 50% ethanol and 3% acetic acid for 30 min, stained with SYPRO Ruby staining solution for 6 hours, and then de-stained in 10% methanol for 30 min. Unlabeled proteins were detected (FIG. 11B) in rows 2 through 7 containing a dilution series of BSA (500 ng, 250 ng, 100 ng, 50 ng, 25 ng, and 10 ng of loaded mass, respectively). Protein quantification in FIG. 11C, was normalized to an internal standard to account for any μlane to μlane variation—100 ng of unlabeled OVA. FIG. 11D shows the resulting device image after the complete 7.5 hour staining procedure. The BSA and OVA peaks were clearly distinguished over the entire mass range with a BSA SNR of 359±26 for the 500 ng samples to 75±10 for the 10 ng sample (n=12). The calibration curve showed a linear relationship across the 10 ng to 100 ng range. The non-linearity at higher mass loads indicated that shorter staining times may be used for linear quantification over the entire mass range, 10 ng to 500 ng. The presently disclosed devices have an open nature of fsPAG, which may facilitate additional downstream analyses including additional assay stages.

Figure 19:
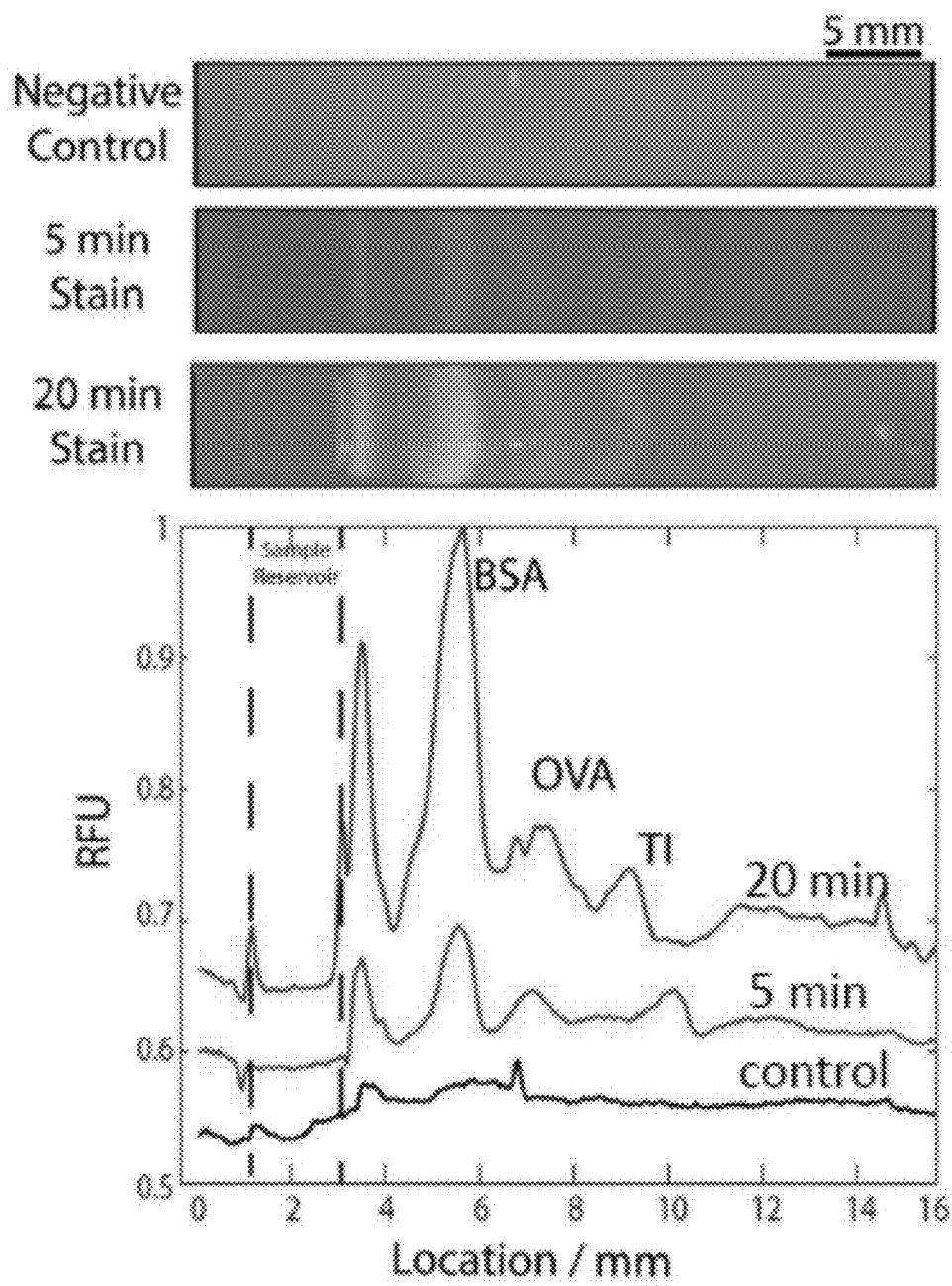
FIG. 19 shows an image (top) and graph (bottom) of the separation and staining of BSA, OVA and TI in a free-standing polyacrylamide microchannel array, according to embodiments of the present disclosure. The proteins were resolved in 1 cm and in 6 minutes using 15% acrylamide and E=60V/cm.

FIG. 19 shows an image (top) and graph (bottom) of the separation and staining of BSA, OVA and TI (670 ng BSA, 450 ng OVA, and 420 ng TI) in a free-standing polyacrylamide microchannel array. The proteins were resolved in 1 cm and in 6 minutes using 15% acrylamide and E=60V/cm. The protocol for the assay was as follows: (1) SDS PAGE was performed using 60 V/cm for 5 min; (2) the gels were soaked in SYPRO Tangerine and 7.5% acetic acid for 5-20 min; and (3) the gels were rinsed in 7.5% acetic acid for 5 min. The assay was completed in about 15-30 minutes. BSA SNR was 92.6 at 5 min, and 203.0 at 20 min. Sensitivity (SNR=10) with a 5 min stain was 72 ng, and 33 ng with a 20 min stain.

Separation Performance in fsPAGE Improved with EOF Suppression Additives

Experiments were performed to determine the effect of reservoir EOF suppression on the subsequent fsPAGE. The separation resolution (RS) of a protein ladder was observed, as shown in FIG. 12. A protein ladder containing 500 nM BSA*, OVA*, and TL* was separated in a 20% T PAG with no EOF suppressor and with 0.5% Triton X-100 in the sample reservoir, as shown in FIGS. 12A and 12B, respectively. Separations were compared in FIG. 12C when OVA* migrated 1 mm along the separation axis. For the fsPAGE separation with no EOF suppressor present, the BSA*-OVA* pair showed RS=0.84 with the OVA*-TI* pair having an RS=0.79. In comparison, when 0.5% Triton x100 was added to the reservoir, the BSA*-OVA* RS was increased by ~30% (RS=1.11), as did the RS of the OVA*-TI* pair (~20% increase to RS=0.94). The peak intensity of the injected sample zones also increased in the Triton x100 experiment: 42% for BSA*, 41% for OVA*, and 16% for TI* (RFU's of 2.55, 2.42 and 0.82 to RFU's of 3.61, 3.15, and 0.95 for BSA*, OVA*, and TI*, respectively).

Figure 13:
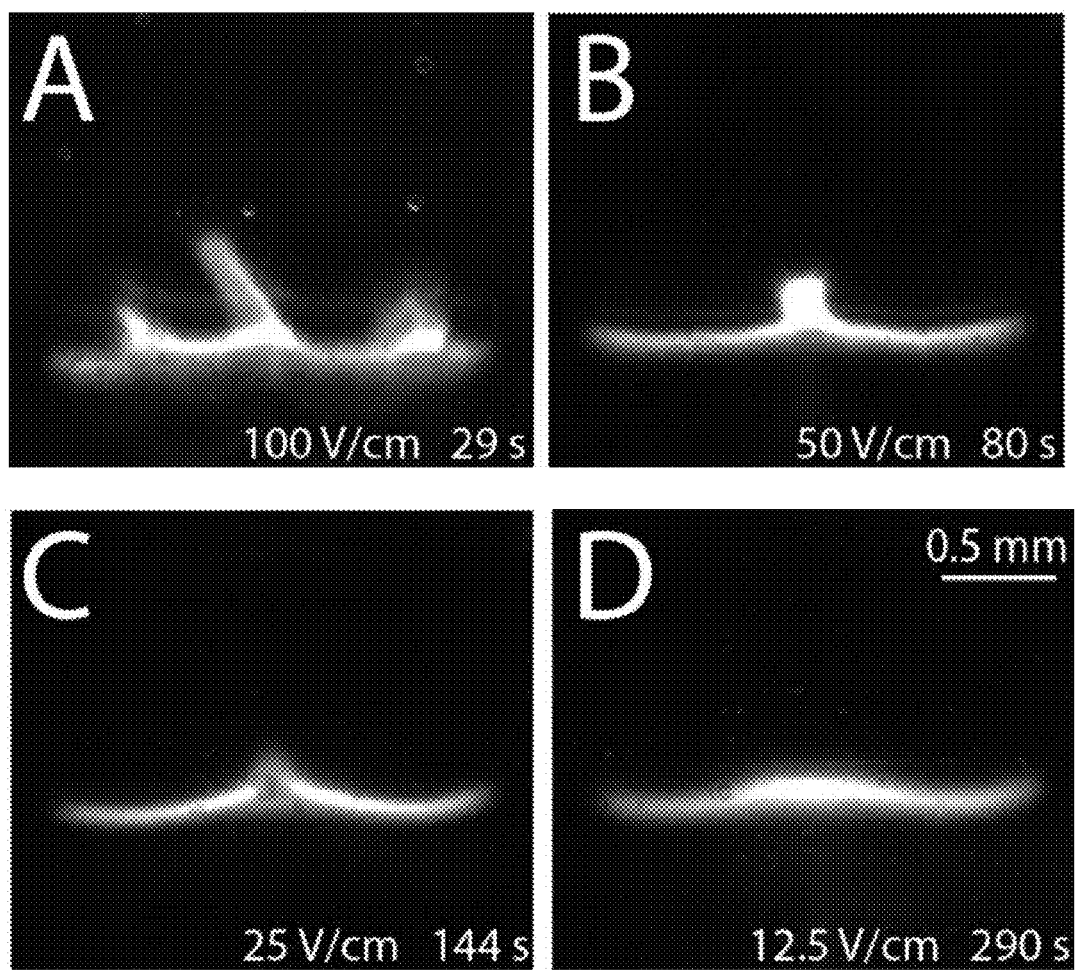
FIGS. 13A-13D show images of discontinuous electrophoresis injection of a 300 nM OVA* from a 1 mm (axial) by 2 mm (transverse) sample reservoir performed at 100 V/cm (FIG. 13A), 50 V/cm (FIG. 13B), 25 V/cm (FIG. 13C), and 12.5 V/cm (FIG. 13D) into a 20% T PAG. With EOF induced dispersion, the band distortion was improved with a lower injection electric field. The reduced injection potential also resulted in longer injection times: 29 s for 100 V/cm, 80 s for 50 V/cm, 144 s for 25 V/cm, and 290 s for 12.5 V/cm.

Lower Injection Potentials Resulted in Less Band Distortion in Discontinuous Electrophoresis During a discontinuous electrophoresis injection in fsPAGE an isotachophoretic stack migrated through the free-solution reservoir. The increased electric field—a result of the isothachophoretic stack—increased EOF and resulted in band distortion when the protein sample was loaded into the PAG at 100 V/cm (FIG. 7B). EOF band dispersion persisted even when an EOF suppressor additive was used (FIG. 7E). In FIG. 13, the band distortion was related to the applied electric field, as expected for dispersive EOF. Band distortion was minimized by using an injection potential of 12.5 V/cm. Reducing the injection potential may result in a slower injection.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A device comprising:
   a support comprising a functionalized surface;
   two or more free-standing, directly photopatterned polymeric separation media covalently attached to the functionalized surface of the support and configured to separate a sample along a directional axis, wherein each polymeric separation medium defines a single, open microchannel, and
   wherein each polymeric separation medium is associated with a sample loading element contiguous with and composed of the same material as the polymeric separation medium.

2. The device of claim 1, wherein the separation medium comprises a polymeric gel.

3. The device of claim 1, wherein the sample-loading element comprises one or more walls defining an interior space of the sample-loading element.

4. The device of claim 1, wherein the polymeric separation medium and the sample-loading element comprise a polymeric gel.

5. The device of claim 1, wherein the device is a microfluidic device.

6. The device of claim 1, wherein each polymeric separation medium is covalently attached to the functionalized surface of the support during a polymerization reaction that forms the polymeric separation medium.

7. The device of claim 6, wherein each polymeric separation medium is formed from gel precursors configured to react with each other, and wherein the polymerization reaction is initiated by exposing the gel precursors to light.

8. A method of detecting an analyte in a fluid sample, the method comprising:
(a) introducing the fluid sample into a device comprising:
(i) a support comprising a functionalized surface;
(ii) two or more free-standing, directly photopatterned polymeric separation media covalently attached to the functionalized surface of the support and configured to separate the sample along a directional axis, wherein each polymeric separation medium defines a single, open microchannel, and
wherein each polymeric separation medium is associated with a sample loading element contiguous with and composed of the same material as the polymeric separation medium;
(b) directing the sample through the polymeric separation medium to produce a separated sample; and
(c) detecting the analyte in the separated sample.

9. The method of claim 8, wherein the directing comprises applying an electric field to the polymeric separation medium.

10. The method of claim 8, wherein the detecting comprises labeling the analyte in the separated sample.

11. The method of claim 8, further comprising contacting the separated sample with one or more secondary reagents.

12. The method of claim 11, wherein the contacting comprises one or more of diffusion, electrokinetic transport and hydrodynamic transport.

13. The method of claim 11, wherein the one or more secondary reagents are selected from the group consisting of an affinity probe, a dye, an antibody, an enzyme, an enzyme substrate and a nucleic acid.

14. The method of claim 8, wherein the device is a microfluidic device.

15. The method of claim 8, wherein the method is performed in 20 min or less.

16. A system comprising:
(a) one or more devices each comprising:
(i) a support comprising a functionalized surface;
(ii) two or more free-standing, directly photopatterned polymeric separation media covalently attached to the functionalized surface of the support and configured to separate a sample along a directional axis, wherein each polymeric separation medium defines a single, open microchannel, and
wherein each polymeric separation medium is associated with a sample loading element contiguous with and composed of the same material as the polymeric separation medium; and
(b) a detector.

17. The system of claim 16, wherein the polymeric separation medium comprises a polymeric gel.

18. The system of claim 16, wherein the one or more devices is a microfluidic device and wherein the system comprises two or more microfluidic devices.

19. The system of claim 18, wherein the microfluidic devices in each region are contiguous and comprise the same material.

20. The system of claim 18, wherein the microfluidic devices in each region are arranged in series.

21. The system of claim 18, wherein the system comprises two or more regions of devices arranged in parallel.

22. The system of claim 16, further comprising a chamber configured to substantially maintain the ambient humidity around the devices.

23. The system of claim 22, wherein the chamber is configured to maintain a higher humidity than ambient conditions.

24. The system of claim 16, wherein the one or more devices is a microfluidic device.

25. A kit comprising:
(a) a device comprising:
(i) a support comprising a functionalized surface;
(ii) two or more free-standing, directly photopatterned polymeric separation media covalently attached to the functionalized surface of the support and configured to separate a sample along a directional axis, wherein each polymeric separation medium defines a single, open microchannel, and
wherein each polymeric separation medium is associated with a sample loading element contiguous with and composed of the same material as the polymeric separation medium; and
(b) a packaging configured to contain the device.

26. The kit of claim 25, wherein the device is a microfluidic device.

* * * * *